(12) United States Patent
Charrier et al.

(10) Patent No.: US 10,137,063 B2
(45) Date of Patent: *Nov. 27, 2018

(54) DYE COMPOSITION COMPRISING NONIONIC GUAR GUM OR A NONIONIC DERIVATIVE THEREOF, PROCESS AND DEVICE FOR THE SAME

(71) Applicant: L'OREAL, Paris (FR)

(72) Inventors: Delphine Charrier, Boulogne Billancourt (FR); Geraldine Fack, Levallois (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/418,699

(22) PCT Filed: Aug. 2, 2013

(86) PCT No.: PCT/EP2013/066268
§ 371 (c)(1),
(2) Date: Jan. 30, 2015

(87) PCT Pub. No.: WO2014/020148
PCT Pub. Date: Feb. 6, 2014

(65) Prior Publication Data
US 2015/0202125 A1  Jul. 23, 2015

Related U.S. Application Data

(60) Provisional application No. 61/698,770, filed on Sep. 10, 2012.

(30) Foreign Application Priority Data

Aug. 2, 2012  (FR) ..................... 12 57543

(51) Int. Cl.
| | | |
|---|---|---|
| *A61Q 5/10* | (2006.01) | |
| *A61K 8/04* | (2006.01) | |
| *A61K 8/31* | (2006.01) | |
| *A61K 8/44* | (2006.01) | |
| *A61K 8/46* | (2006.01) | |
| *A61K 8/73* | (2006.01) | |
| *A61K 8/86* | (2006.01) | |
| *A61K 8/41* | (2006.01) | |
| *B65D 83/14* | (2006.01) | |

(52) U.S. Cl.
CPC .............. *A61K 8/046* (2013.01); *A61K 8/31* (2013.01); *A61K 8/415* (2013.01); *A61K 8/44* (2013.01); *A61K 8/463* (2013.01); *A61K 8/737* (2013.01); *A61K 8/86* (2013.01); *A61Q 5/10* (2013.01); *B65D 83/752* (2013.01); *A61K 2800/4324* (2013.01); *A61K 2800/5422* (2013.01); *A61K 2800/5424* (2013.01); *A61K 2800/5428* (2013.01); *A61K 2800/596* (2013.01); *A61K 2800/87* (2013.01)

(58) Field of Classification Search
CPC .......... A61Q 5/10; A61K 8/463; A61K 8/737; A61K 8/86; A61K 8/415; A61K 8/046; A61K 8/44; A61K 2800/596; A61K 2800/5428; A61K 2800/87; A61K 2800/5424; A61K 2800/5422
USPC ........................................... 8/405
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,798,053 A | 7/1957 | Brown |
| 2,923,692 A | 2/1960 | Ackerman et al. |
| 2,961,347 A | 11/1960 | Floyd |
| 3,100,739 A | 8/1963 | Kaiser et al. |
| 3,206,462 A | 9/1965 | McCarty |
| 3,227,615 A | 1/1966 | Korden |

(Continued)

FOREIGN PATENT DOCUMENTS

| | | |
|---|---|---|
| DE | 2359399 A1 | 6/1975 |
| DE | 2527638 A1 | 5/1976 |

(Continued)

OTHER PUBLICATIONS

STIC Search Report dated Aug. 5, 2015.*

(Continued)

*Primary Examiner* — Eisa B Elhilo

(74) *Attorney, Agent, or Firm* — The Marbury Law Group, PLLC

(57) ABSTRACT

The present invention relates to a composition for dyeing human keratin fibers such as the hair, in mousse form, comprising: (a) at least one oxidation dye precursor; (b) at least one amphoteric or zwitterionic surfactant; (c) at least a second surfactant chosen from nonionic and anionic surfactants, or mixtures thereof; (d) at least one fatty substance; (e) at least one nonionic guar gum. The invention also relates to a process for dyeing human keratin fibers, in which is applied a composition preferably in foam form, obtained by mixing the above mentioned composition, free of oxidizing agent other than atmospheric oxygen, with a composition comprising at least one oxidizing agent other than atmospheric oxygen, and also to a suitable multi-compartment device.

24 Claims, No Drawings

(56) References Cited

U.S. PATENT DOCUMENTS

| | | |
|---|---|---|
| 3,524,842 A | 8/1970 | Grossmann et al. |
| 3,578,386 A | 5/1971 | Kalopissis et al. |
| 3,589,978 A | 6/1971 | Kamal et al. |
| 3,617,163 A | 11/1971 | Kalopissis et al. |
| 3,632,559 A | 1/1972 | Matter et al. |
| 3,665,036 A | 5/1972 | Kalopissis et al. |
| 3,709,437 A | 1/1973 | Wright |
| 3,817,698 A | 6/1974 | Kalopissis et al. |
| 3,867,456 A | 2/1975 | Kalopissis et al. |
| 3,869,454 A | 3/1975 | Lang et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,937,364 A | 2/1976 | Wright |
| 3,955,918 A | 5/1976 | Lang |
| 3,966,904 A | 6/1976 | Green et al. |
| 3,985,499 A | 10/1976 | Lang et al. |
| 3,986,825 A | 10/1976 | Sokol |
| 4,001,432 A | 1/1977 | Green et al. |
| 4,003,699 A | 1/1977 | Rose et al. |
| 4,005,193 A | 1/1977 | Green et al. |
| 4,013,787 A | 3/1977 | Varlerberghe et al. |
| 4,022,351 A | 5/1977 | Wright |
| 4,025,301 A | 5/1977 | Lang |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,075,136 A | 2/1978 | Schaper |
| 4,117,914 A | 10/1978 | Snyder |
| 4,131,576 A | 12/1978 | Iovine et al. |
| 4,147,306 A | 4/1979 | Bennett |
| 4,151,162 A | 4/1979 | Lang et al. |
| 4,157,388 A | 6/1979 | Christiansen |
| 4,165,367 A | 8/1979 | Chakrabarti |
| 4,166,894 A | 9/1979 | Schaper |
| 4,172,887 A | 10/1979 | Vanlerberghe et al. |
| RE30,199 E | 1/1980 | Rose et al. |
| 4,184,615 A | 1/1980 | Wright |
| 4,189,468 A | 2/1980 | Vanlerberghe et al. |
| 4,197,865 A | 4/1980 | Jacquet et al. |
| 4,223,009 A | 9/1980 | Chakrabarti |
| 4,226,784 A | 10/1980 | Kalopissis et al. |
| 4,237,243 A | 12/1980 | Quack et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,422,853 A | 12/1983 | Jacquet et al. |
| 4,509,949 A | 4/1985 | Huang et al. |
| 4,579,732 A | 4/1986 | Grollier et al. |
| 4,591,610 A | 5/1986 | Grollier |
| 4,598,862 A | 7/1986 | Rice |
| 4,608,250 A | 8/1986 | Jacquet et al. |
| 4,615,467 A | 10/1986 | Grogan et al. |
| 4,702,906 A | 10/1987 | Jacquet et al. |
| 4,719,282 A | 1/1988 | Nadolsky et al. |
| 4,761,273 A | 8/1988 | Grollier et al. |
| 4,777,040 A | 10/1988 | Grollier et al. |
| 4,804,385 A | 2/1989 | Grollier et al. |
| 4,886,517 A | 12/1989 | Bugaut et al. |
| 4,948,579 A | 8/1990 | Jacquet et al. |
| 4,970,066 A | 11/1990 | Grollier et al. |
| 5,061,289 A | 10/1991 | Clausen et al. |
| 5,196,189 A | 3/1993 | Jacquet et al. |
| 5,364,031 A | 11/1994 | Taniguchi et al. |
| 5,380,340 A | 1/1995 | Neunhoeffer et al. |
| 5,422,031 A | 6/1995 | Nomura et al. |
| 5,534,267 A | 7/1996 | Neunhoeffer et al. |
| 5,663,366 A | 9/1997 | Neunhoeffer et al. |
| 5,670,471 A | 9/1997 | Amalric et al. |
| 5,685,882 A | 11/1997 | Samain et al. |
| 5,708,151 A | 1/1998 | Mockli |
| 5,766,576 A | 6/1998 | Lowe et al. |
| 5,879,413 A | 3/1999 | Pengilly et al. |
| 5,888,252 A | 3/1999 | Mockli |
| 5,919,273 A | 7/1999 | Rondeau et al. |
| 5,944,360 A | 8/1999 | Crapart |
| 5,993,490 A | 11/1999 | Rondeau et al. |
| 6,045,591 A | 4/2000 | Deneulenaere |
| 6,099,592 A | 8/2000 | Vidal et al. |
| 6,120,780 A | 9/2000 | Dupuis et al. |
| 6,136,042 A | 10/2000 | Maubru |
| 6,179,881 B1 | 1/2001 | Henrion et al. |
| 6,284,003 B1 | 9/2001 | Rose et al. |
| 6,338,741 B1 | 1/2002 | Vidal et al. |
| 6,458,167 B1 | 10/2002 | Genet et al. |
| 6,492,502 B2 | 12/2002 | Henrion et al. |
| 6,497,730 B1 | 12/2002 | Genet et al. |
| 6,645,258 B2 | 11/2003 | Vidal et al. |
| 6,689,922 B1 | 2/2004 | Bernardon |
| 6,730,789 B1 | 5/2004 | Birault et al. |
| 6,797,013 B1 | 9/2004 | Lang et al. |
| 6,863,883 B1 | 3/2005 | Tsujino et al. |
| 7,125,427 B2 | 10/2006 | Schmenger et al. |
| 8,066,781 B2 | 11/2011 | Hercouet et al. |
| 8,147,564 B2 | 4/2012 | Deconinck et al. |
| 8,236,063 B2 | 8/2012 | Reichert et al. |
| 8,889,110 B2 | 11/2014 | Braida-Valerio et al. |
| 2001/0001332 A1 | 5/2001 | Henrion et al. |
| 2002/0010970 A1* | 1/2002 | Cottard ................ A61K 8/342 8/405 |
| 2002/0050013 A1 | 5/2002 | Vidal et al. |
| 2002/0165368 A1 | 11/2002 | Henrion et al. |
| 2003/0019051 A9 | 1/2003 | Vidal et al. |
| 2004/0098815 A1 | 5/2004 | Schmenger et al. |
| 2006/0000032 A1 | 1/2006 | Knuebel et al. |
| 2006/0070191 A1 | 4/2006 | Lang et al. |
| 2010/0154136 A1 | 6/2010 | Hercouet et al. |
| 2010/0158844 A1 | 6/2010 | Braida-Valerio et al. |
| 2010/0162493 A1 | 7/2010 | Audousset et al. |
| 2010/0175202 A1* | 7/2010 | Simonet ................ A61K 8/22 8/408 |
| 2011/0033407 A1* | 2/2011 | Krueger ................ A61K 8/97 424/70.9 |
| 2011/0155166 A1 | 6/2011 | Deconinck et al. |
| 2012/0048288 A1 | 3/2012 | Reichert et al. |
| 2012/0276029 A1 | 11/2012 | Ascione et al. |

FOREIGN PATENT DOCUMENTS

| | | |
|---|---|---|
| DE | 2538363 A1 | 5/1976 |
| DE | 3843892 A1 | 6/1990 |
| DE | 4133957 A1 | 4/1993 |
| DE | 4137005 A1 | 5/1993 |
| DE | 4220388 A1 | 12/1993 |
| DE | 19543988 A1 | 5/1997 |
| DE | 20114179 U1 | 10/2001 |
| DE | 102006012575 A1 | 2/2007 |
| DE | 1020090903002 A1 | 11/2010 |
| DE | 102011017519 A1 | 10/2012 |
| EP | 0080976 A1 | 6/1983 |
| EP | 0122324 A1 | 10/1984 |
| EP | 0173109 A2 | 3/1986 |
| EP | 0216479 A1 | 4/1987 |
| EP | 0395282 A2 | 10/1990 |
| EP | 0503853 A2 | 9/1992 |
| EP | 0531943 A1 | 3/1993 |
| EP | 0714954 A2 | 6/1996 |
| EP | 0770375 A1 | 5/1997 |
| EP | 0815828 A1 | 1/1998 |
| EP | 0823250 A2 | 2/1998 |
| EP | 0850636 A1 | 7/1998 |
| EP | 0850637 A1 | 7/1998 |
| EP | 0860636 A1 | 8/1998 |
| EP | 0918053 A1 | 5/1999 |
| EP | 0920856 A1 | 6/1999 |
| EP | 1062940 A1 | 12/2000 |

(56) References Cited

FOREIGN PATENT DOCUMENTS

| | | |
|---|---|---|
| EP | 1123693 A2 | 8/2001 |
| EP | 1133975 A2 | 9/2001 |
| EP | 2014275 A2 | 1/2009 |
| EP | 2198923 A2 | 6/2010 |
| EP | 2198929 A1 | 6/2010 |
| EP | 2272493 A1 | 1/2011 |
| EP | 2340807 A2 | 7/2011 |
| FR | 1221122 A | 5/1960 |
| FR | 1516943 A | 2/1968 |
| FR | 1540423 A | 8/1968 |
| FR | 1567219 A | 5/1969 |
| FR | 1583363 A | 10/1969 |
| FR | 2077143 A | 10/1971 |
| FR | 2080759 A1 | 11/1971 |
| FR | 2162025 A1 | 7/1973 |
| FR | 2189006 A1 | 1/1974 |
| FR | 2190406 A2 | 2/1974 |
| FR | 2252840 A1 | 6/1975 |
| FR | 2270846 A1 | 12/1975 |
| FR | 2275462 A1 | 1/1976 |
| FR | 2280361 A2 | 2/1976 |
| FR | 2285851 A1 | 4/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2393573 A1 | 1/1979 |
| FR | 2413907 A1 | 8/1979 |
| FR | 2416723 A1 | 9/1979 |
| FR | 2505348 A1 | 11/1982 |
| FR | 2542997 A1 | 9/1984 |
| FR | 2570946 A1 | 4/1986 |
| FR | 2722687 A1 | 1/1996 |
| FR | 1560664 A | 3/1996 |
| FR | 2733749 A1 | 11/1996 |
| FR | 2757385 A1 | 6/1998 |
| FR | 2788433 A1 | 7/2000 |
| FR | 2801308 A1 | 5/2001 |
| FR | 2886136 A1 | 12/2006 |
| FR | 2940066 A1 | 6/2010 |
| FR | 2954092 A1 | 6/2011 |
| FR | 2954095 A1 | 6/2011 |
| GB | 738585 A | 10/1955 |
| GB | 1026978 A | 4/1966 |
| GB | 1153196 A | 5/1969 |
| GB | 1163385 A | 9/1969 |
| GB | 1195386 A | 6/1970 |
| GB | 1514466 A | 6/1978 |
| GB | 1546809 A | 5/1979 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 97/44004 A1 | 11/1997 |
| WO | 98/44012 A1 | 10/1998 |
| WO | 99/36047 A1 | 7/1999 |
| WO | 99/48465 A1 | 9/1999 |
| WO | 00/26167 A1 | 5/2000 |
| WO | 01/66646 A1 | 9/2001 |
| WO | 03/020229 A2 | 3/2003 |
| WO | 03/029359 A1 | 4/2003 |
| WO | 2006/125619 A1 | 11/2006 |
| WO | WO 2008/049768 A1 * | 5/2008 | ............... A16K 8/42 |
| WO | WO 2010/133640 A2 * | 11/2010 | ............... A61K 8/41 |
| WO | WO 2011/009563 A2 * | 11/2011 | ............... A61K 8/04 |
| WO | 2014/020145 A1 | 2/2014 |
| WO | 2014/020146 A2 | 2/2014 |
| WO | 2014/020147 A2 | 2/2014 |
| WO | 2014108433 A1 | 7/2014 |

OTHER PUBLICATIONS

International Search Report and Written Opinion for PCT/EP2013/066268, dated Sep. 25, 2013.
International Search Report and Written Opinion for co-pending PCT/EP2013/066266 (WO 2014/020147A2), dated May 15, 2014.
International Search Report for co-pending PCT/EP2013/066263 (WO 20141020145A2), dated October 18, 2013.
International Search Report and Written Opinion for co-pending PCT/EP2013/066264 (WO 20141020146A2), dated Nov. 4, 2014.
English language abstract for DE 4137005A1 (May 13, 1993).
English language Abstract for DE 4220388A1 (Dec. 23, 1993).
English language Abstract for DE 102006012575A1. (Feb. 8, 2007).
English language Abstract for EP 0080976A1 (Jun. 8, 1983).
English language Abstract for EP 0770375A1 (May 2, 1997).
English language Abstract for EP 1123693A2 (Aug. 16, 2001).
English language Abstract for EP 2014276A2 (Jan. 14, 2009).
English language Abstract for FR 2886136A1 (EP1728500) (Dec. 1, 2006).
English language Abstract for FR 2940066A1 (Jun. 25, 2010).
English language Abstract for JP 02-019576A (Jan. 23, 1990).
English language Abstract for JP 05-163124A (Jun. 29, 1993).
Porter, M.R., "Handbook of Surfactants," published by Blackie & Son (Glasgow and London), 1991, pp. 116-178.
Todd, Charles, et al., "Volatile Silicone Fluids for Cosmetic Formulations," Cosmetics and Toiletries, vol. 91, Jan. 1976, pp. 29-32.
International Search Report for PCT/EP2014/050210, dated May 20, 2014.
Non-Final Office Action for co-pending U.S. Appl. No. 14/418,736, dated Nov. 20, 2015.
Final Office Action for co-pending U.S. Appl. No. 14/418,736, dated Jun. 2, 2016.
Non-Final Office Action for co-pending U.S. Appl. No. 14/418,746, dated Dec. 22, 2015.
Final Office Action for co-pending U.S. Appl. No. 14/418,746, dated Jul. 11, 2016.
Non-Final Office Action for co-pending U.S. Appl. No. 14/418,762, dated Dec. 22, 2015.
Non-Final Office Action for co-pending U.S. Appl. No. 14/758,985, dated Jan. 22, 2016.
Final Office Action for co-pending U.S. Appl. No. 14/418,762, dated Jul. 18, 2016.

* cited by examiner

DYE COMPOSITION COMPRISING NONIONIC GUAR GUM OR A NONIONIC DERIVATIVE THEREOF, PROCESS AND DEVICE FOR THE SAME

This is a national stage application of PCT/EP2013/066268, filed internationally on Aug. 2, 2013, which claims priority to U.S. Provisional Application No. 61/698,770, filed on Sep. 10, 2012; as well as French Application 1257543, filed on Aug. 2, 2012.

The present invention relates to a dye composition comprising oxidation dye precursors, at least one amphoteric or zwitterionic surfactant, at least one nonionic or anionic surfactant, and at least one nonionic guar gum, and also to a dyeing process using a mixture in foam form obtained from the said composition, free of oxidizing agent, which is mixed with an oxidizing composition before application. The invention also relates to suitable multi-compartment devices.

Among the methods for dyeing human keratin fibres, such as the hair, mention may be made of oxidation dyeing or permanent dyeing. More particularly, this form of dyeing uses one or more oxidation dyes, usually one or more oxidation bases optionally combined with one or more couplers.

In general, the oxidation bases are chosen from ortho- or para-phenylenediamines, ortho or para-aminophenols and heterocyclic compounds. These oxidation bases are colourless or weakly coloured compounds which, when combined with oxidizing products, can give access to coloured entities.

The shades obtained with these oxidation bases are often varied by combining them with one or more couplers, these couplers being chosen especially from aromatic meta-diamines, meta-aminophenols, meta-diphenols and certain heterocyclic compounds, such as indole compounds.

The variety of the molecules used as oxidation bases and couplers allows a rich range of colours to be obtained.

Permanent dyeing processes thus consist in using, with the dye composition, an aqueous composition comprising at least one oxidizing agent, such as hydrogen peroxide, under alkaline pH conditions in the vast majority of cases. The alkaline agent conventionally used is aqueous ammonia or other alkaline agents, such as alkanolamines.

The dye compositions applied to the fibres (thus comprising the oxidizing agent) may be in various forms such as lotions, gels, emulsions, creams or foams.

Dyeing foams are pleasant to use, but they have drawbacks. Thus, they often have poor staying power over time. For example, rapid disappearance of the foam after application may be observed. Moreover, they can often lead to non-uniform application along the fibres.

There is a real need to develop oxidation dye compositions which, firstly, before being mixed with the oxidizing composition, have suitable rheology, and which, after mixing with the oxidizing agent, produce a good foam texture and the foam remains sufficiently stable over time, with good working qualities once applied, while at the same time retaining efficient dyeing properties, especially in terms of build-up and homogeneity of the coloration obtained.

This aim and others are achieved by the present invention, one subject of which is thus a composition for dyeing human keratin fibres, such as the hair, comprising:
 (a) at least one oxidation dye precursor;
 (b) at least one amphoteric or zwitterionic surfactant;
 (c) at least a second surfactant chosen from nonionic and anionic surfactants, or mixtures thereof;
 (d) at least one fatty substance other than ceramides;
 (e) at least one nonionic guar gum.

The invention also relates to a process for dyeing human keratin fibres, in which is applied a composition preferably in foam form, obtained by mixing the abovementioned dye composition, free of oxidizing agent, with a composition comprising at least one oxidizing agent other than atmospheric oxygen.

Similarly, a subject of the invention is a non-aerosol multi-compartment device comprising the said dye composition free of oxidizing agent; an oxidizing composition and optionally a foam dispenser, which may be equipped with a mechanical pumping system, comprising a dispensing system for delivering the mixture of the two abovementioned compositions, in the form of a foam.

The invention similarly relates to an aerosol device comprising a means for producing, in foam form, a composition comprising the abovementioned dye composition and an oxidizing composition.

The composition of the invention, free of oxidizing agent (other than atmospheric oxygen), is in the form of a product of creamy texture, which, when mixed with the oxidizing composition, produces a foam that is particularly pleasant to apply. This foam has a light, airy texture, which makes it particularly pleasant to use. The qualities of the foam are sufficiently long-lasting to enable uniform application of the dye product, without running.

The composition of the invention makes it possible to obtain good dyeing properties, such as strength of the colour, resistance to external agents (shampooing, perspiration, light) and homogeneity, which are particularly efficient.

Other characteristics and advantages of the invention will emerge more clearly on reading the description and the examples that follow.

In the text hereinbelow, and unless otherwise indicated, the limits of a range of values are included in that range.

The term "at least one" associated with an ingredient of the composition signifies "one or more".

The human keratin fibres treated by means of the process according to the invention are preferably the hair.

Dyes

As indicated previously, the dye composition according to the invention comprises at least one oxidation dye precursor.

As oxidation dye precursors, use may be made of oxidation bases and couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-paraphenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Mention may be made, among the bis(phenyl)alkylenediamines, by way of example, of N,N'-bis(β-hydroxyethyl)-N,N'-bis(4'-aminophenyl)-1,3-diaminopropanol, N,N'-bis (β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis (4-aminophenyl)tetramethylenediamine, N,N'-bis(4-methylaminophenyl)tetramethylenediamine, N,N'-bis (ethyl)-N,N'-bis(4'-amino-3'-methylphenyl) ethylenediamine, 1,8-bis(2,5-diaminophenoxy)-3,6-dioxaoctane and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases, mention may be made, by way of example, of pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases of use in the present invention are the 3-aminopyrazolo[1,5-a]pyridine oxidation bases or the addition salts thereof described, for example, in patent application FR 2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo [1,5-a]pyrid-3-ylamine, (3-aminopyrazolo[1,5-a]pyrid-7-yl) methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1, 5-a]pyridine, 3,4-diaminopyrazolo[1,5-a]pyridine, pyrazolo [1,5-a]pyridine-3,7-diamine, 7-(morpholin-4-yl)pyrazolo[1, 5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, and the addition salts thereof.

Mention may be made, among the pyrimidine derivatives, of the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives, examples that may be mentioned include 3,4-diaminopyrazole, 4-amino-1,3-dimethyl-5-hydrazinopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof.

According to another variant, the heterocyclic oxidation bases are chosen from diaminodiazacyclopentene derivatives comprising in their molecular structure the following substructure:

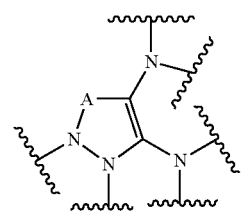

A denoting a carbonyl group or a carbon atom bearing a hydrogen atom or another substituent.

These compounds may or may not be salified.

Preferably, the diaminodiazacyclopentene derivative(s) are chosen from diaminopyrazolone derivatives, diaminopyrazole derivatives, or mixtures thereof.

The term "diaminopyrazolone derivative(s)" means a compound or compounds comprising in their molecular structure the following substructure:

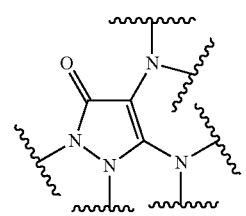 [SMILES: *N(*)c1c(N(*)*)n(*)n(*)c1=O]

These compounds may or may not be salified.

The diaminopyrazolone derivatives are 4,5-diaminopyrazol-3-one or 2,3-diaminopyrazol-1-one derivatives.

The diaminopyrazolone derivative(s) are preferably chosen from the compounds of general formula (I) below, or salts thereof:

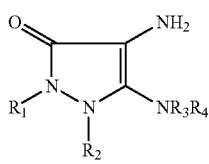

(I)

in which:
R$_1$, R$_2$, R$_3$ and R$_4$, which may be identical or different, represent, independently of each other:
a hydrogen atom;
a linear or branched C$_1$-C$_{10}$, preferably C$_1$-C$_6$, alkyl group, optionally substituted with one or more groups chosen from OR$_5$, NR$_6$R$_7$ and carboxy groups, sulfonic, carboxamido CONR$_6$R$_7$ and sulfonamido SO$_2$NR$_6$R$_7$ groups, aliphatic heterocycles such as piperidine, aryls optionally substituted with one or more group(s) chosen from C$_1$-C$_4$ alkyl, hydroxyl, C$_1$-C$_2$ alkoxy, amino and (di)(C$_1$-C$_2$)alkylamino groups;
an aryl group optionally substituted with one or more group(s) chosen from C$_1$-C$_4$ alkyl, hydroxyl, C$_1$-C$_2$ alkoxy, amino and (di)(C$_2$-C$_2$)alkylamino groups;
a 5- or 6-membered heteroaryl group, optionally substituted by one or more group(s) chosen from C$_1$-C$_4$ alkyl and C$_1$-C$_2$ alkoxy groups;
R$_5$, R$_6$ and R$_7$, which may be identical or different, represent:
a hydrogen atom;
a linear or branched C$_1$-C$_4$, preferably C$_1$-C$_2$, alkyl group, optionally substituted with one or more group(s) chosen from hydroxyl, C$_1$-C$_2$ alkoxy, carboxamido CONR$_8$R$_9$, and sulfonyl SO$_2$R$_8$ groups, aryl optionally substituted with a C$_1$-C$_4$ alkyl, hydroxyl, C$_1$-C$_2$ alkoxy, amino or (di)(C$_1$-C$_2$)alkylamino group;
an aryl group optionally substituted with one or more group(s) chosen from C$_1$-C$_4$ alkyl, hydroxyl, C$_1$-C$_2$ alkoxy, amino and (di)(C$_1$-C$_2$)alkylamino groups;
a carboxamido CONR$_8$R$_9$ group;
a sulfonyl SO$_2$R$_8$ group;
R$_8$ and R$_9$, which may be identical or different, represent a hydrogen atom; a linear or branched C$_1$-C$_4$ alkyl group, optionally substituted with one or more group(s) chosen from hydroxyl and C$_1$-C$_2$ alkoxy groups;
R$_1$ and R$_2$, on the one hand, and R$_3$ and R$_4$, on the other hand, may also form, together with the nitrogen atom(s) to which they are attached, a saturated or unsaturated 5- to 7-membered heterocycle, which is optionally substituted or N-substituted with one or more group(s) chosen from halogen atoms, amino, (di)(C$_1$-C$_4$)alkylamino, (di)hydroxy(C$_1$-C$_2$)alkylamino, hydroxyl, carboxy, carboxamido, (di)(C$_1$-C$_2$)alkylcarboxamido and C$_1$-C$_2$ alkoxy groups and C$_1$-C$_4$ alkyl groups optionally substituted with one or more groups chosen from hydroxyl, amino, (di)alkylamino, alkoxy, carboxy and sulfonyl groups; the said heterocycles formed by R$_1$ and R$_2$, on the one hand, and R$_3$ and R$_4$, on the other hand, with the nitrogen atom(s) to which they are attached, possibly being identical or different, and the ring members forming the said heterocycles possibly being chosen, preferably, from carbon, nitrogen and oxygen atoms.

According to one particular embodiment, R$_1$ and R$_2$, which may be identical or different, are chosen, independently of each other, from:
a C$_1$-C$_6$ alkyl group optionally substituted with one or more group(s) chosen from hydroxyl, C$_1$-C$_2$ alkoxy, amino and (di)(C$_1$-C$_2$)alkylamino groups; and
a phenyl, methoxyphenyl, ethoxyphenyl or benzyl group.
Preferably, R$_1$ and R$_2$, which may be identical or different, are chosen, independently of each other, from methyl, ethyl, 2-hydroxyethyl, 3-hydroxypropyl, 2-hydroxypropyl and phenyl groups.
According to another embodiment, R$_1$ and R$_2$ form, together with the nitrogen atoms to which they are attached, a saturated or unsaturated 5- or 6-membered ring, optionally substituted with one or more group(s) chosen from halogen atoms, amino, (di)(C$_1$-C$_4$)alkylamino, (di)hydroxy(C$_1$-C$_2$)alkylamino, hydroxyl, carboxy, carboxamido, (di)(C$_1$-C$_2$)alkylcarboxamido and C$_1$-C$_2$ alkoxy groups, and C$_1$-C$_4$ alkyl groups optionally substituted with one or more group(s) chosen from hydroxyl, amino, (di)alkylamino, alkoxy, carboxy and sulfonyl groups.
Preferably, R$_1$ and R$_2$ form, together with the nitrogen atoms to which they are attached, a pyrazolidine or pyridazolidine ring, optionally substituted with one or more group(s) chosen from C$_1$-C$_4$ alkyl, hydroxyl, C$_1$-C$_2$ alkoxy, carboxy, carboxamido, amino and (di)(C$_1$-C$_2$)alkylamino groups.
Preferably, R$_1$ and R$_2$ form, together with the nitrogen atoms to which they are attached, a pyrazolidine or pyridazolidine ring, optionally substituted with one or more groups chosen from C$_1$-C$_4$ alkyl, hydroxyl, C$_1$-C$_2$ alkoxy, carboxy, carboxamido, amino and (di)(C$_1$-C$_2$)alkylamino groups.
Even more advantageously, R$_1$ and R$_2$ form, together with the nitrogen atoms to which they are attached, a pyrazolidine, pyridazoline or pyridazolidine ring.
As regards R$_3$ and R$_4$, these radicals, which may be identical or different, are more particularly chosen from a hydrogen atom; a linear or branched C$_1$-C$_6$ alkyl group, optionally substituted with one or more group(s) chosen from hydroxyl, C$_1$-C$_2$ alkoxy, amino, (di)(C$_1$-C$_2$)alkylamino groups and aliphatic heterocycles such as piperidine; a phenyl group optionally substituted with one or more groups chosen from hydroxyl, amino and C$_1$-C$_2$ alkoxy groups.
Preferably, R$_3$ and R$_4$, which may be identical or different, are chosen from a hydrogen atom and a methyl, ethyl, isopropyl, 2-hydroxyethyl, 3-hydroxypropyl, 2-hydroxypropyl and 2-carboxyethyl, 2-dimethylaminoethyl, pyrrolidin-1-yl, 3-hydroxypyrrolidin-1-yl, 4-piperidin-1-yl, 4-methylpiperidin-1-yl and 3-dimethylaminopiperidin-1-yl group.
According to one particular embodiment, the R$_3$ and R$_4$ groups represent a hydrogen atom.
According to another embodiment, R$_3$ and R$_4$ form, together with the nitrogen atom to which they are attached, a 5- to 7-membered ring chosen from pyrrolidine, piperidine, homopiperidine, piperazine and homopiperazine heterocycles; the said ring possibly being substituted or N-substituted with one or more group(s) chosen from hydroxyl, amino, (di)(C$_1$-C$_2$)alkylamino, (di)hydroxy(C$_1$-C$_2$)alkylamino, carboxy, carboxamido, (di)(C$_1$-C$_2$)alkylcarboxamido and C$_1$-C$_4$ alkyl groups optionally substituted with one or more group(s) chosen from hydroxyl, amino and (di)(C$_1$-C$_2$)alkylamino groups.
More particularly, R$_3$ and R$_4$ form, together with the nitrogen atom to which they are attached, a 5- to 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 2-hydroxypiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine and N-(2-hydroxyethyl)homopiperazine.

Preferably, $R_3$ and $R_4$ form, together with the nitrogen atom to which they are attached, a 5- to 7-membered ring chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, hydroxypiperidine, homopiperidine, 1,4-diazepane, N-methylhomopiperazine and N-β-hydroxyethylhomopiperazine.

In accordance with an even more preferred embodiment of the invention, $R_3$ and $R_4$ form, together with the nitrogen atom to which they are attached, a 5-membered ring such as pyrrolidine, 3-hydroxypyrrolidine, 3-aminopyrrolidine or 3-dimethylaminopyrrolidine.

The compounds of formula (I) may be optionally salified with strong mineral acids, for instance HCl, HBr, HI, $H_2SO_4$ or $H_3PO_4$, or organic acids, for instance acetic acid, lactic acid, tartaric acid, citric acid, succinic acid, benzenesulfonic acid, para-toluenesulfonic acid, formic acid or methanesulfonic acid.

They may also be in the form of solvates, for example a hydrate or a solvate of a linear or branched alcohol such as ethanol or isopropanol.

As examples of derivatives of formula (I), mention may be made of the compounds below, and the addition salts thereof:
4,5-diamino-1,2-dimethyl-1,2-dihydropyrazol-3-one;
4-amino-5-methylamino-1,2-dimethyl-1,2-dihydropyrazol-3-one;
4-amino-5-dimethylamino-1,2-dimethyl-1,2-dihydropyrazol-3-one;
4-amino-5-(2-hydroxyethyl)amino-1,2-dimethyl-1,2-dihydropyrazol-3-one;
4-amino-5-(pyrrolidin-1-yl)-1,2-dimethyl-1,2-dihydropyrazol-3-one;
4-amino-5-(piperidin-1-yl)-1,2-dimethyl-1,2-dihydropyrazol-3-one;
4,5-diamino-1,2-bis(2-hydroxyethyl)-1,2-dihydropyrazol-3-one;
4-amino-5-methylamino-1,2-bis(2-hydroxyethyl)-1,2-dihydropyrazol-3-one;
4-amino-5-dimethylamino-1,2-bis(2-hydroxyethyl)-1,2-dihydropyrazol-3-one;
4-amino-5-(2-hydroxyethyl)amino-1,2-bis(2-hydroxyethyl)-1,2-dihydropyrazol-3-one;
4-amino-5-(pyrrolidin-1-yl)-1,2-bis(2-hydroxyethyl)-1,2-dihydropyrazol-3-one;
4-amino-5-(piperidin-1-yl)-1,2-bis(2-hydroxyethyl)-1,2-dihydropyrazol-3-one;
4,5-diamino-1,2-diethyl-1,2-dihydropyrazol-3-one;
4,5-diamino-1,2-diphenyl-1,2-dihydropyrazol-3-one;
4,5-diamino-1-ethyl-2-methyl-1,2-dihydropyrazol-3-one;
4,5-diamino-2-ethyl-1-methyl-1,2-dihydropyrazol-3-one;
4,5-diamino-1-phenyl-2-methyl-1,2-dihydropyrazol-3-one;
4,5-diamino-2-phenyl-1-methyl-1,2-dihydropyrazol-3-one;
4,5-diamino-1-(2-hydroxyethyl)-2-methyl-1,2-dihydropyrazol-3-one;
4,5-diamino-2-(2-hydroxyethyl)-1-methyl-1,2-dihydropyrazol-3-one;
2,3-diamino-6,7-dihydro-1H,5H-pyrazolo[1,2-a]pyrazol-1-one;
2-amino-3-methylamino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(2-hydroxyethyl)amino-6,7-dihydro-1H,5H-pyrazolo[1,2-a]pyrazol-1-one;
2-amino-3-(2-hydroxypropyl)amino-6,7-dihydro-1H,5H-pyrazolo[1,2-a]pyrazol-1-one;
2-amino-3-bis(2-hydroxyethyl)amino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
2-amino-3-(3-hydroxypyrrolidin-1-yl)-6,7-dihydro-1H,5H-pyrazolo[1,2-a]pyrazol-1-one;
2-amino-3-(piperidin-1-yl)-6,7-dihydro-1H,5H-pyrazolo[1,2-a]pyrazol-1-one;
2,3-diamino-6-hydroxy-6,7-dihydro-1H,5H-pyrazolo[1,2-a]pyrazol-1-one;
2,3-diamino-6-methyl-6,7-dihydro-1H,5H-pyrazolo[1,2-a]pyrazol-1-one;
2,3-diamino-6,6-dimethyl-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
2,3-diamino-5,8-dihydro-1H,6H-pyridazino[1,2-a]pyrazol-1-one;
4-amino-5-dimethylamino-1,2-diethyl-1,2-dihydropyrazol-3-one;
4-amino-1,2-diethyl-5-ethylamino-1,2-dihydropyrazol-3-one;
4-amino-1,2-diethyl-5-isopropylamino-1,2-dihydropyrazol-3-one;
4-amino-1,2-diethyl-5-(2-hydroxyethylamino)-1,2-dihydropyrazol-3-one;
4-amino-5-(2-dimethylaminoethylamino)-1,2-diethyl-1,2-dihydropyrazol-3-one;
4-amino-5-[bis(2-hydroxyethyl)amino]-1,2-diethyl-1,2-dihydropyrazol-3-one;
4-amino-1,2-diethyl-5-(3-imidazol-1-ylpropylamino)-1,2-dihydropyrazol-3-one;
4-amino-1,2-diethyl-5-(3-hydroxypyrrolidin-1-yl)-1,2-dihydropyrazol-3-one;
4-amino-5-pyrrolidin-1-yl-1,2-diethyl-1,2-dihydropyrazol-3-one;
4-amino-5-(3-dimethylaminopyrrolidin-1-yl)-1,2-diethyl-1,2-dihydropyrazol-3-one;
4-amino-1,2-diethyl-5-(4-methylpiperazin-1-yl)pyrazolidin-3-one;
some of which are featured below to illustrate the names via chemical structures:

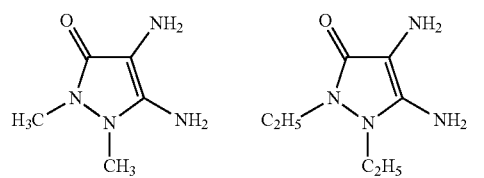

4,5-diamino-1,2-dimethyl-1,2-dihydropyrazol-3-one

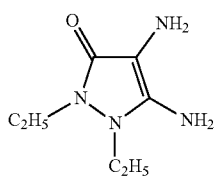

4,5-diamino-1,2-diethyl-1,2-dihydropyrazol-3-one

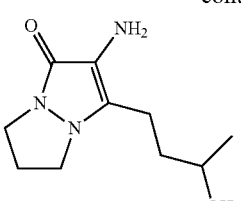

2-amino-3-(2-hydroxypropyl)amino-6,7-dihydro-1H,5H-pyrazolo[1,2-a]pyrazol-1-one

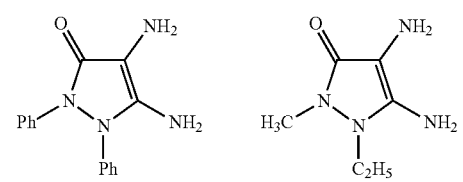

4,5-diamino-1,2-diphenyl-1,2-dihydropyrazol-3-one

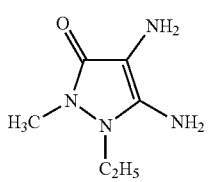

4,5-diamino-1-ethyl-2-methyl-1,2-dihydropyrazol-3-one

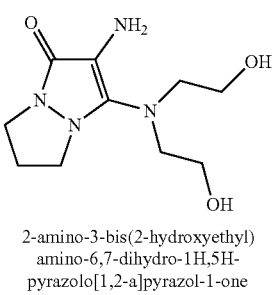

2-amino-3-bis(2-hydroxyethyl)amino-6,7-dihydro-1H,5H-pyrazolo[1,2-a]pyrazol-1-one

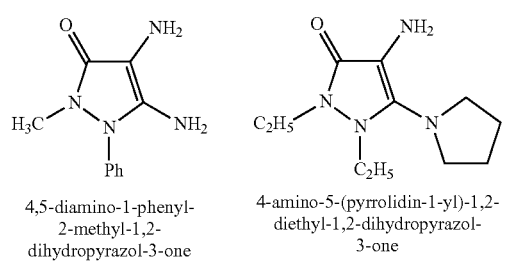

4,5-diamino-1-phenyl-2-methyl-1,2-dihydropyrazol-3-one

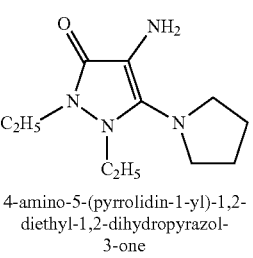

4-amino-5-(pyrrolidin-1-yl)-1,2-diethyl-1,2-dihydropyrazol-3-one

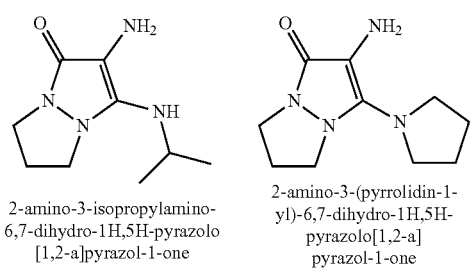

2-amino-3-isopropylamino-6,7-dihydro-1H,5H-pyrazolo[1,2-a]pyrazol-1-one 2-amino-3-(pyrrolidin-1-yl)-6,7-dihydro-1H,5H-pyrazolo[1,2-a]pyrazol-1-one

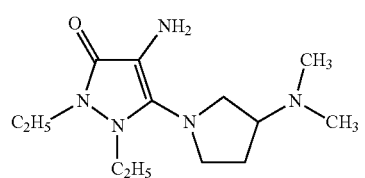

4-amino-5-(3-dimethylaminopyrrolidin-1-yl)-1,2-diethyl-1,2-dihydropyrazol-3-one

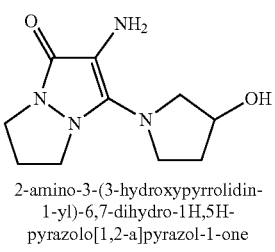

2-amino-3-(3-hydroxypyrrolidin-1-yl)-6,7-dihydro-1H,5H-pyrazolo[1,2-a]pyrazol-1-one

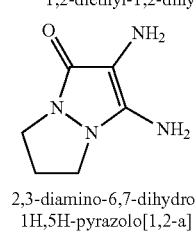

2,3-diamino-6,7-dihydro-1H,5H-pyrazolo[1,2-a]pyrazol-1-one 2-amino-3-methylamino-6,7-dihydro-1H,5H-pyrazolo[1,2-a]pyrazol-1-one

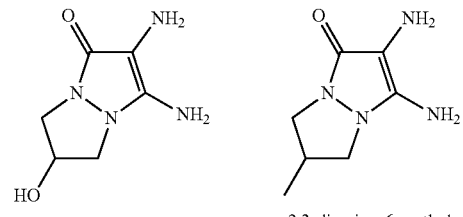

2,3-diamino-6-hydroxy-6,7-dihydro-1H,5H-pyrazolo[1,2-a]pyrazol-1-one 2,3-diamino-6-methyl-6,7-dihydro-1H,5H-pyrazolo[1,2-a]pyrazol-1-one

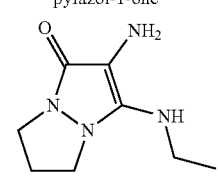

2-amino-3-ethylamino-6,7-dihydro-1H,5H-pyrazolo[1,2-a]pyrazol-1-one

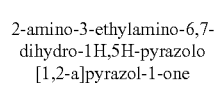

2-amino-3-(2-hydroxyethyl)amino-6,7-dihydro-1H,5H-pyrazolo[1,2-a]pyrazol-1-one

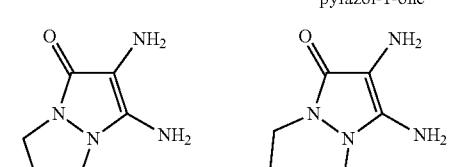
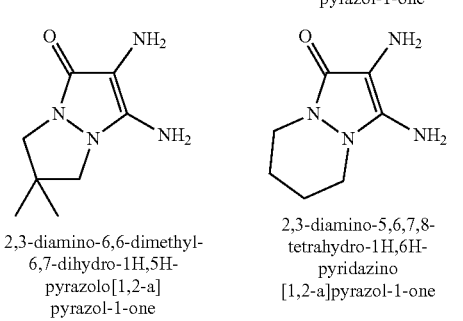
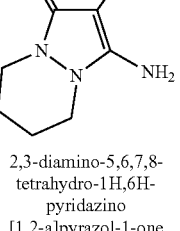

2,3-diamino-6,6-dimethyl-6,7-dihydro-1H,5H-pyrazolo[1,2-a]pyrazol-1-one 2,3-diamino-5,6,7,8-tetrahydro-1H,6H-pyridazino[1,2-a]pyrazol-1-one -continued

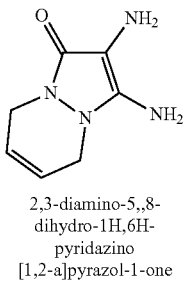

2,3-diamino-5,,8-
dihydro-1H,6H-
pyridazino
[1,2-a]pyrazol-1-one

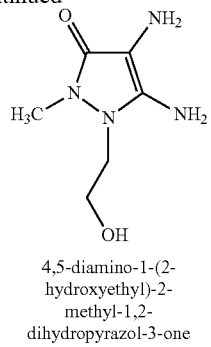

4,5-diamino-1-(2-
hydroxyethyl)-2-
methyl-1,2-
dihydropyrazol-3-one

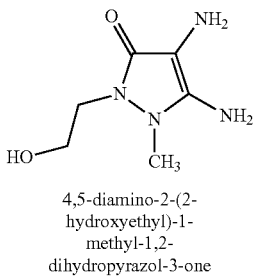

4,5-diamino-2-(2-
hydroxyethyl)-1-
methyl-1,2-
dihydropyrazol-3-one

Among these compounds, the diaminopyrazolone derivatives of formula (I) that are particularly preferred are the following:
2,3-diamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
4,5-diamino-1,2-dimethyl-1,2-dihydropyrazol-3-one;
4,5-diamino-1,2-diethyl-1,2-dihydropyrazol-3-one;
4,5-diamino-1,2-bis(2-hydroxyethyl)-1,2-dihydropyrazol-3-one;
2-amino-3-(2-hydroxyethyl)amino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
4-amino-1,2-diethyl-5-pyrrolidin-1-yl-1,2-dihydropyrazol-3-one;
4-amino-5-(3-dimethylaminopyrrolidin-1-yl)-1,2-diethyl-1,2-dihydropyrazol-3-one;
2,3-diamino-6-hydroxy-6,7-dihydro-1H,5H-pyrazolo[1,2-a]pyrazol-1-one.

Even more particularly preferred is 2,3-diamino-6,7-dihydro-1H,5H-pyrazolo[1,2-a]pyrazol-1-one and salts thereof, such as 2,3-diamino-6,7-dihydro-1H,5H-pyrazolo[1,2-a]pyrazol-1-one dimethane sulfonate, of formula:

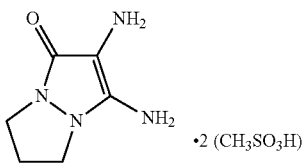 [SMILES: Nc1c(N)n2n(c1=O)CCC2]

The term "diaminopyrazole derivative(s)" is intended to mean a compound or compounds comprising in its (or their) molecular structure the following substructure:

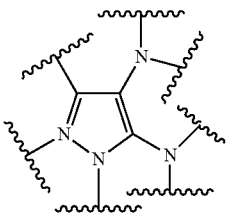

These compounds may or may not be salified.

The diaminopyrazole derivative is therefore a 4,5-diaminopyrazole derivative.

The diaminopyrazole derivative(s) according to the invention are preferably chosen from the compounds of general formula (II) below, or salts thereof:

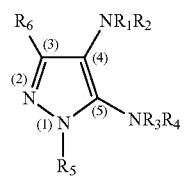

in which:
$R_1$, $R_2$, $R_3$, $R_4$ and $R_5$, which may be identical or different, represent a hydrogen atom or; a $C_1$-$C_6$ alkyl radical which is unsubstituted or substituted with at least one substituent chosen from OR, NHR, NRR', SR, SOR, $SO_2R$, COR, COOH, $CONH_2$, CONHR, CONRR', $PO(OH)_2$, SH, $SO_3X$, a non-cationic heterocycle, Cl, Br or I, X denoting a hydrogen atom, Na, K or $NH_4$, and R and R', which may be identical or different, representing a $C_1$-$C_4$ alkyl or alkenyl; a $C_2$-$C_4$ hydroxyalkyl radical; a $C_2$-$C_4$ aminoalkyl radical; a phenyl radical; a phenyl radical substituted with a halogen atom or a $C_1$-$C_4$ alkyl, $C_1$-$C_4$ alkoxy, nitro, trifluoromethyl, amino or $C_1$-$C_4$ alkylamino radical; a benzyl radical; a benzyl radical substituted with a halogen atom or with a $C_1$-$C_4$ alkyl, $C_1$-$C_4$ alkoxy, methylenedioxy or amino radical; a radical

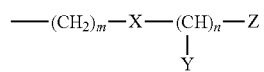

in which m and n are integers, which may be identical or different, between 0 and 3 inclusive, X represents an oxygen atom or even the NH group, Y represents a hydrogen atom or a $C_1$-$C_4$ alkyl radical, and Z represents a methyl radical when n is equal to 0, or Z represents a $C_1$-$C_4$ alkyl radical or a group OR NR"R'" when n is greater than or equal to 1, R" and R'", which may be identical or different, denoting a hydrogen atom or a $C_1$-$C_4$ alkyl radical; or $R_9$ forms, with the nitrogen atom of the group $NR_7R_8$ in position 5, a heterocycle that is at least 4-membered,
$R_6$ represents a $C_1$-$C_6$ alkyl radical; a $C_1$-$C_4$ hydroxyalkyl radical; a $C_1$-$C_4$ aminoalkyl radical; a ($C_1$-$C_4$)alkylamino($C_1$-$C_4$)alkyl radical; a di($C_1$-$C_4$)alkylamino ($C_1$-$C_4$)alkyl radical; a hydroxy($C_1$-$C_4$)alkylamino($C_1$-$C_4$)alkyl radical; a ($C_1$-$C_4$)alkoxymethyl radical; a phenyl radical; a phenyl radical substituted with a halogen atom or with a ($C_1$-$C_4$)alkyl, ($C_1$-$C_4$)alkoxy, nitro, trifluoromethyl, amino or ($C_1$-$C_4$)alkylamino radical; a benzyl radical; a benzyl radical substituted with a halogen atom or with a ($C_1$-$C_4$)alkyl, ($C_1$-$C_4$) alkoxy, nitro, trifluoromethyl, amino or ($C_1$-$C_4$)alkylamino radical; a heterocycle chosen from thiophene, furan and pyridine, or else a —$(CH_2)_p$—O—$(CH_2)_q$—OR" radical, in which p and q are integers, which may be identical or different, between 1 and 3 inclusively and R" is as defined previously, it being understood that at least one of the radicals $R_1$, $R_2$, $R_3$ and $R_4$ represents a hydrogen atom.

The compounds of formula (II) may optionally be salified with strong mineral acids, for instance HCl, HBr, HI, $H_2SO_4$ or $H_3PO_4$, or organic acids, for instance acetic acid, lactic acid, tartaric acid, citric acid, succinic acid, benzenesulfonic acid, para-toluenesulfonic acid, formic acid or methanesulfonic acid.

They may also be in the form of solvates, for example a hydrate or a solvate of a linear or branched alcohol such as ethanol or isopropanol.

As examples of derivatives of formula (II) usable according to the invention, mention may be made of the compounds described in patents DE-A-38 43 892 and DE-A-41 33 957 and patent applications WO 94/08969, WO 94/08970, FR-A-2 733 749 and DE-A-195 43 988, for instance 4,5-diamino-1-methylpyrazole, 4,5-diamino-1-(2-hydroxyethyl)pyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole and 4-amino-5-(2'-aminoethyl)amino-1,3-dimethylpyrazole, and the addition salts thereof.

Preference is given even more particularly to 4,5-diamino-1-(2-hydroxyethyl)-1H-pyrazole and salts thereof, such as 4,5-diamino-1-(2-hydroxyethyl)-1H-pyrazole sulfate, having the following formula:

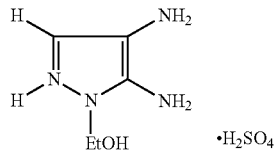

Among the couplers that may be used in the composition according to the invention, mention may be made in particular of meta-phenylenediamines, meta-aminophenols, meta-diphenols, naphthalene-based couplers and heterocyclic couplers, for instance indole derivatives, indoline derivatives, sesamol and derivatives thereof, pyridine derivatives, pyrazolotriazole derivatives, pyrazolones, indazoles, benzimidazoles, benzothiazoles, benzoxazoles, 1,3-benzodioxoles, quinolines, and the addition salts of these compounds with an acid.

These couplers are more particularly chosen from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, the addition salts thereof with an acid, and mixtures thereof.

The addition salts of the oxidation bases and couplers are especially chosen from the addition salts with an acid such as the hydrochlorides, hydrobromides, sulfates, phosphates, citrates, succinates, tartrates, lactates, tosylates, benzenesulfonates, para-toluenesulfonates, formates and acetates.

The oxidation base(s) are generally each present in an amount from 0.0001% to 10% by weight relative to the total weight of the dye composition and preferably from 0.005% to 5% by weight relative to the total weight of the composition.

The coupler(s) each generally represent from 0.0001% to 10% by weight relative to the total weight of the composition and preferably from 0.005% to 5% by weight relative to the total weight of the dye composition.

The dye composition used in the process according to the invention may optionally comprise synthetic or natural, cationic or nonionic, direct dyes.

Examples of particularly suitable direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanine direct dyes, porphyrin direct dyes and natural direct dyes, alone or as mixtures. In particular, mention may be made of direct dyes from among: azo; methine; carbonyl; azine; nitro (hetero)aryl; tri(hetero)arylmethane; porphyrin; phthalocyanine and natural direct dyes, alone or as mixtures.

When they are present, the direct dye(s) more particularly represent from 0.0001% to 10% by weight of the total weight of the dye composition and preferably from 0.005% to 5% by weight.

Amphoteric or Zwitterionic Surfactants

The dye composition according to the invention also comprises at least one amphoteric or zwitterionic surfactant.

In particular, the amphoteric or zwitterionic surfactant(s), which are preferably non-silicone, which are usable in the present invention may especially be derivatives of optionally quaternized aliphatic secondary or tertiary amines, in which derivatives the aliphatic group is a linear or branched chain comprising from 8 to 22 carbon atoms, the said amine derivatives comprising at least one anionic group, for instance a carboxylate, sulfonate, sulfate, phosphate or phosphonate group.

Mention may be made in particular of $(C_8-C_{20})$alkylbetaines, $(C_8-C_{20})$alkylsulfobetaines, $(C_8-C_{20})$alkylamido $(C_3-C_8)$alkylbetaines and $(C_8-C_{20})$alkylamido$(C_6-C_8)$alkylsulfobetaines.

Among the optionally quaternized secondary or tertiary aliphatic amine derivatives that can be used, as defined above, mention may also be made of the compounds of respective structures (B1) and (B2) below:

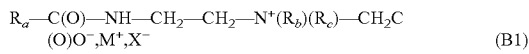

$$R_a—C(O)—NH—CH_2—CH_2—N^+(R_b)(R_c)—CH_2C(O)O^-,M^+,X^- \quad (B1)$$

in which formula:
$R_a$ represents a $C_{10}-C_{30}$ alkyl or alkenyl group derived from an acid $R_a$COOH preferably present in hydrolysed coconut oil, or a heptyl, nonyl or undecyl group;
$R_b$ represents a β-hydroxyethyl group; and
$R_c$ represents a carboxymethyl group;
$M^+$ represents a cationic counterion derived from an alkali metal or alkaline-earth metal, such as sodium, an ammonium ion or an ion derived from an organic amine, and
$X^-$ represents an organic or mineral anionic counterion, such as that chosen from halides, acetates, phosphates, nitrates, $(C_1-C_4)$alkyl sulfates, $(C_1-C_4)$alkyl- or $(C_1-C_4)$alkylarylsulfonates, in particular methyl sulfate and ethyl sulfate; or alternatively $M^+$ and $X^-$ are absent;

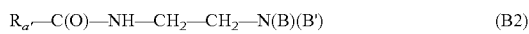

$$R_{a'}—C(O)—NH—CH_2—CH_2—N(B)(B') \quad (B2)$$

in which formula:
B represents the group —$CH_2$—$CH_2$—O—X';
B' represents the group —$(CH_2)_z$Y', with z=1 or 2;
X' represents the group —$CH_2$—C(O)OH, —$CH_2$—C(O)OZ', —$CH_2$—$CH_2$—C(O)OH, —$CH_2$—$CH_2$—C(O)OZ', or a hydrogen atom;
Y' represents the group —C(O)OH, —C(O)OZ', —$CH_2$—CH(OH)—$SO_3$H or the group —$CH_2$—CH(OH)—$SO_3$—Z';
Z' represents a cationic counterion derived from an alkali metal or alkaline-earth metal, such as sodium, an ammonium ion or an ion derived from an organic amine;
$R_{a'}$ represents a $C_{10}-C_{30}$ alkyl or alkenyl group of an acid $R_{a'}$—C(O)OH preferably present in hydrolysed linseed oil or coconut oil, an alkyl group, especially of $C_{17}$ and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Use may also be made of compounds of formula (B'2):

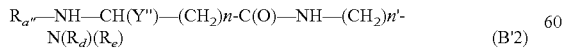

$$R_{a''}—NH—CH(Y'')—(CH_2)n-C(O)—NH—(CH_2)n'-N(R_d)(R_e) \quad (B'2)$$

in which formula:
Y'' represents the group —C(O)OH, —C(O)OZ'', —$CH_2$—CH(OH)—$SO_3$H or the group —$CH_2$—CH(OH)—$SO_3$—Z'';
$R_d$ and $R_e$ represent, independently of each other, a $C_1-C_4$ alkyl or hydroxyalkyl radical;
Z'' represents a cationic counterion derived from an alkali metal or alkaline-earth metal, such as sodium, an ammonium ion or an ion derived from an organic amine;
$R_{a''}$ represents a $C_{10}-C_{30}$ alkyl or alkenyl group of an acid $R_{a''}$C(O)OH preferably present in hydrolysed linseed oil or coconut oil; and
n and n', independently of each other, denote an integer ranging from 1 to 3.

Among the compounds of formula (B'2), mention may be made of the compound classified in the CTFA dictionary under the name sodium diethylaminopropyl cocoaspartamide and sold by the company Chimex under the name Chimexane HB.

Among the amphoteric or zwitterionic surfactants mentioned above, use is preferably made of $(C_8-C_{20})$alkylbetaines such as cocylbetaine, $(C_8-C_{20})$alkylamido$(C_3-C_8)$ alkylbetaines such as cocamidopropylbetaine, and mixtures thereof, and the compounds of formula (B'2), such as the sodium salt of diethylaminopropyl laurylaminosuccinamate (INCI name: sodium diethylaminopropyl cocoaspartamide).

More preferentially, the amphoteric or zwitterionic surfactant(s) are chosen from cocamidopropylbetaine and cocylbetaine, the sodium salt of diethylaminopropyl laurylaminosuccinamate, or mixtures thereof.

In accordance with one advantageous embodiment of the invention, the content of amphoteric or zwitterionic surfactant(s) ranges from 0.1% to 30% by weight, preferably from 0.5% to 20% by weight and more preferably from 1% to 10% by weight, relative to the total weight of the composition.

Second Surfactant(s)

The composition according to the invention also comprises at least a second surfactant chosen from nonionic and anionic surfactants, or mixtures thereof.

Examples of nonionic surfactants that may be used in the dye composition used according to the invention are described, for example, in the *Handbook of Surfactants* by M. R. Porter, published by Blackie & Son (Glasgow and London), 1991, pp. 116-178.

Examples of nonionic second surfactants that may be mentioned include oxyalkylenated, or glycerolated, nonionic surfactants, in particular the following surfactants, alone or as mixtures:

oxyalkylenated $(C_8-C_{24})$alkylphenols;
saturated or unsaturated, linear or branched, oxyalkylenated or glycerolated $C_8-C_{30}$ alcohols;
saturated or unsaturated, linear or branched, oxyalkylenated $C_8-C_{30}$ amides;
esters of saturated or unsaturated, linear or branched, $C_8-C_{30}$ acids and of polyethylene glycols;
esters of saturated or unsaturated, linear or branched, $C_8-C_{30}$ acids and of sorbitol, which are preferably oxyethylenated;
fatty acid esters of sucrose;
$(C_8-C_{30})$alkylpolyglycosides, $(C_8-C_{30})$alkenylpolyglycosides, which are optionally oxyalkylenated (0 to 10 oxyalkylenated units) and which comprise 1 to 15 glucose units, $(C_8-C_{30})$alkylglucoside esters;
saturated or unsaturated, oxyethylenated plant oils;
condensates of ethylene oxide and/or of propylene oxide, inter alia, alone or as mixtures;
N—$(C_8-C_{30})$alkylglucamine derivatives and N—$(C_8-C_{30})$acylmethylglucamine derivatives;
aldobionamides;
amine oxides;
oxyethylenated and/or oxypropylenated silicones.

The oxyalkylene units are more particularly oxyethylene or oxypropylene units, or a combination thereof, preferably oxyethylene units.

The number of moles of ethylene oxide and/or of propylene oxide preferably ranges from 1 to 100 and more particularly from 2 to 50; the number of moles of glycerol ranges in particular from 1 to 30.

Advantageously, the nonionic surfactants do not comprise oxypropylenated units.

By way of example of glycerolated nonionic surfactants, use may preferably be made of monoglycerolated or polyglycerolated $C_8$-$C_{40}$ alcohols comprising from 1 to 30 mol of glycerol, preferably from 1 to 10 mol of glycerol.

Examples of compounds of this type that may be mentioned include lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

Among the glycerolated alcohols, it is more particularly preferred to use $C_8/C_{10}$ alcohol containing 1 mol of glycerol, $C_{10}/C_{12}$ alcohol containing 1 mol of glycerol and $C_{12}$ alcohol containing 1.5 mol of glycerol.

According to a preferred embodiment of the invention, the nonionic surfactant(s), if they are present, are chosen from:
  oxyethylenated $C_8$-$C_{30}$ alcohols comprising from 1 to 100 mol of ethylene oxide, preferably from 2 to 50, and more particularly from 2 to 30 mol of ethylene oxide;
  saturated or unsaturated, oxyethylenated plant oils comprising from 1 to 100 mol of ethylene oxide, preferably from 2 to 50;
  ($C_8$-$C_{30}$)alkylpolyglycosides, which are optionally oxyalkylenated (0 to 10 OE) and which comprise 1 to 15 glucose units;
  monoglycerolated or polyglycerolated $C_8$-$C_{40}$ alcohols comprising from 1 to 30 mol of glycerol, preferably from 1 to 10 mol of glycerol.

The term "anionic surfactant" means a surfactant comprising, as ionic or ionizable groups, only anionic groups. These anionic groups are preferably chosen from the groups —C(O)OH, —C(O)O$^-$, —SO$_3$H, —S(O)$_2$O$^-$, —OS(O)$_2$OH, —OS(O)$_2$O$^-$, —P(O)OH$_2$, —P(O)$_2$O$^-$, —P(O)O$_2^-$, —P(OH)$_2$, =P(O)OH, —P(OH)O$^-$, =P(O)O$^-$, =POH and =PO$^-$, the anionic parts comprising a cationic counterion such as an alkali metal, an alkaline-earth metal or an ammonium.

As examples of anionic second surfactants that may be used in the dye composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffinsulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyl taurates, salts of alkyl monoesters of polyglycoside-polycarboxylic acids, acyl lactylates, salts of D-galactosideuronic acids, salts of alkyl ether carboxylic acids, salts of alkylaryl ether carboxylic acids, salts of alkylamido ether carboxylic acids, and the corresponding non-salified forms of all these compounds, the alkyl and acyl groups of all these compounds comprising from 6 to 40 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts, and in particular sodium or magnesium salts, are preferably used.

Use is preferably made, among the additional anionic surfactants mentioned, of ($C_6$-$C_{24}$)alkyl sulfates, ($C_6$-$C_{24}$) alkyl ether sulfates comprising from 2 to 50 ethylene oxide units, in particular in the form of alkali metal, ammonium, amino alcohol and alkaline-earth metal salts, or a mixture of these compounds.

In particular, it is preferable to use ($C_{12}$-$C_{20}$)alkyl sulfates, ($C_{12}$-$C_{20}$)alkyl ether sulfates comprising from 2 to 20 ethylene oxide units, in particular in the form of alkali metal, ammonium, amino alcohol and alkaline-earth metal salts, or a mixture of these compounds. Better still, it is preferred to use sodium lauryl ether sulfate containing 2.2 mol of ethylene oxide.

According to a particular embodiment of the invention, the content of nonionic or anionic second surfactant(s) ranges from 0.1% to 30% by weight, preferably from 1% to 20% by weight, and more preferably from 1% to 10% by weight, relative to the total weight of the composition.

Fatty Substances Other than Ceramides

As has been mentioned, the composition of the invention comprises one or more fatty substances.

The term "fatty substance" means an organic compound that is insoluble in water at ordinary temperature (25° C.) and at atmospheric pressure (760 mmHg) (solubility of less than 5%, preferably less than 1% and even more preferentially less than 0.1%). They have in their structure at least one hydrocarbon-based chain containing at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The fatty substances of the invention do not comprise salified carboxylic acid groups.

In particular, the fatty substances of the invention are not (poly)oxyalkylenated or (poly)glycerolated ethers.

The term "oil" is intended to mean a "fatty substance" that is liquid at room temperature (25° C.) and at atmospheric pressure (760 mmHg).

The term "non-silicone oil" means an oil not containing any silicon (Si) atoms and the term "silicone oil" means an oil containing at least one silicon atom.

More particularly, the fatty substances are chosen from $C_6$-$C_{16}$ hydrocarbons, hydrocarbons containing more than 16 carbon atoms, non-silicone oils of animal origin, plant oils of triglyceride type, synthetic triglycerides, fluoro oils, fatty alcohols, fatty acid and/or fatty alcohol esters other than triglycerides and plant waxes, non-silicone waxes and silicones, and mixtures thereof.

It should be remembered that fatty alcohols, esters and acids more particularly exhibit at least one saturated or unsaturated and linear or branched hydrocarbon-based group which comprises from 6 to 30 and better still from 8 to 30 carbon atoms and which is optionally substituted, in particular with one or more hydroxyl groups (in particular 1 to 4). If they are unsaturated, these compounds may comprise one to three conjugated or unconjugated carbon-carbon double bonds.

As regards the $C_6$-$C_{16}$ hydrocarbons, they are linear, branched or optionally cyclic, and are preferably alkanes. Examples that may be mentioned include hexane, dodecane and isoparaffins such as isohexadecane and isodecane.

Mention may be made, as hydrocarbon-based oils of animal origin, of perhydrosqualene.

The triglyceride oils of plant or synthetic origin are preferably chosen from liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil.

The linear or branched hydrocarbons of mineral or synthetic origin having more than 16 carbon atoms are preferably chosen from liquid paraffins, petroleum jelly, liquid petroleum jelly, polydecenes or hydrogenated polyisobutene, such as Parleam@.

As regards the $C_6$-$C_{16}$ alkanes, they are linear, branched or optionally cyclic. By way of example, mention may be made of hexane, dodecane and isoparaffins such as isohexadecane and isodecane.

As oils of animal, plant, mineral or synthetic origin that may be used in the composition of the invention, examples that may be mentioned include:
fluoro oils which may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or alternatively bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols which are suitable for the implementation of the invention are more particularly chosen from saturated or unsaturated and linear or branched alcohols comprising from 6 to 30 carbon atoms and preferably from 8 to 30 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

As regards the fatty acid and/or fatty alcohol esters, which are advantageously different from the triglycerides mentioned above, mention may be made in particular of esters of saturated or unsaturated and linear or branched $C_1$-$C_{26}$ aliphatic monoacids or polyacids and of saturated or unsaturated and linear or branched $C_1$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, use is preferably made of ethyl, isopropyl, myristyl, cetyl or stearyl palmitate, 2-ethylhexyl palmitate, 2-octyldecyl palmitate, alkyl myristates, such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates, arachidonates or mixtures thereof, such as, in particular, oleate/palmitate, oleate/stearate or palmitate/stearate mixed esters.

More particularly, use is made of monoesters and diesters and in particular mono- or di-oleate, -stearate, -behenate, -oleopalmitate, -linoleate, -linolenate or -oleostearate of sucrose, of glucose or of methylglucose.

An example that may be mentioned is the product sold under the name Glucate® DO by the company Amerchol, which is a methylglucose dioleate.

Examples of esters or mixtures of esters of sugar and of fatty acid that may also be mentioned include:
  the products sold under the names F160, F140, F110, F90, F70 and SL40 by the company Crodesta, respectively denoting sucrose palmitate/stearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
  the products sold under the name Ryoto Sugar Esters, for example referenced B370 and corresponding to sucrose behenate formed from 20% monoester and 80% diester-triester-polyester;
  the sucrose monopalmitate/stearate-dipalmitate/stearate sold by the company Goldschmidt under the name Tegosoft® PSE.

The non-silicone wax(es) are chosen in particular from carnauba wax, candelilla wax, esparto wax, paraffin wax, ozokerite, plant waxes, such as olive tree wax, rice wax, hydrogenated jojoba wax or absolute flower waxes, such as the blackcurrant blossom essential wax sold by the company Bertin (France), or animal waxes, such as beeswaxes or modified beeswaxes (cerabellina); other waxes or waxy starting materials which can be used according to the invention are in particular marine waxes, such as that sold by the company Sophim under the reference M82, polyethylene waxes or polyolefin waxes in general.

The silicones that can be used in the dye composition according to the present invention are volatile or non-volatile, cyclic, linear or branched silicones, which are unmodified or modified by organic groups, having a viscosity from $5 \times 10^{-6}$ to 2.5 m$^2$/s at 25° C., and preferably $1 \times 10^{-5}$ to 1 m$^2$/s.

The silicones that may be used in accordance with the invention may be in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from amino groups and alkoxy groups.

Organopolysiloxanes are defined in greater detail in Walter Noll's "Chemistry and Technology of Silicones" (1968), Academic Press. They may be volatile or non-volatile.

When they are volatile, the silicones are more particularly chosen from those having a boiling point of between 60° C. and 260° C., and more particularly still from:
  (i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

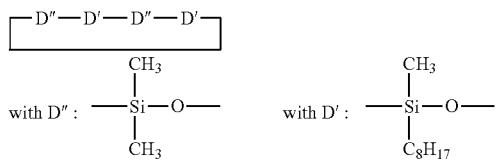

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;
  (ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, "Volatile Silicone Fluids for Cosmetics".

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes having trimethylsilyl end groups. The viscosity of the silicones is measured at 25° C. according to Standard ASTM 445 Appendix C.

Mention may be made, among these polydialkylsiloxanes, without limitation, of the following commercial products:
  the Silbione® oils of the 47 and 70 047 series or the Mirasil® oils sold by Rhodia, for instance the oil 70 047 V 500 000;
  the oils of the Mirasil® series sold by the company Rhodia;
  the oils of the 200 series from the company Dow Corning, such as DC200 with a viscosity of 60 000 mm$^2$/s;
  the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of 48 series from the company Rhodia.

In this category of polydialkylsiloxanes, mention may also be made of the products sold under the names Abil Wax® 9800 and 9801 by the company Goldschmidt, which are polydi($C_1$-$C_{20}$)alkylsiloxanes.

The silicone gums that may be used in accordance with the invention are in particular polydialkylsiloxanes and preferably polydimethylsiloxanes with high number-average molecular weights of between 200 000 and 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products which can be used more particularly in accordance with the invention are mixtures such as:
- the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by the company Dow Corning;
- the mixtures of a polydimethylsiloxane gum and of a cyclic silicone, such as the product SF 1214 Silicone Fluid from the company General Electric; this product is a gum SF 30 corresponding to a dimethicone, having a number-average molecular weight of 500 000, dissolved in the oil SF 1202 Silicone Fluid corresponding to decamethylcyclopentasiloxane;
- mixtures of two PDMSs with different viscosities, and more particularly of a PDMS gum and a PDMS oil, such as the product SF 1236 from the company General Electric. The product SF 1236 is a mixture of a gum SE 30 defined above, with a viscosity of 20 m$^2$/s, and of an oil SF 96 with a viscosity of $5\times10^{-6}$ m$^2$/s. This product preferably comprises 15% of gum SE 30 and 85% of an oil SF 96.

The organopolysiloxane resins that may be used in accordance with the invention are crosslinked siloxane systems containing the following units:

$R_2SiO_{2/2}$, $R_3SiO_{1/2}$, $RSiO_{3/2}$ and $SiO_{4/2}$ in which R represents an alkyl containing 1 to 16 carbon atoms. Among these products, those that are particularly preferred are those in which R denotes a $C_1$-$C_4$ lower alkyl group, more particularly methyl.

Mention may be made, among these resins, of the product sold under the name Dow Corning 593 or those sold under the names Silicone Fluid SS 4230 and SS 4267 by the company General Electric, which are silicones of dimethyl/trimethylsiloxane structure.

Mention may also be made of the resins of the trimethylsiloxysilicate type, sold in particular under the names X22-4914, X21-5034 and X21-5037 by the company Shin-Etsu.

The organomodified silicones that can be used in accordance with the invention are silicones as defined above and comprising in their structure one or more organofunctional groups attached via a hydrocarbon-based group.

In addition to the silicones described above, the organomodified silicones can be polydiarylsiloxanes, in particular polydiphenylsiloxanes, and polyalkylarylsiloxanes functionalized by the abovementioned organofunctional groups.

The polyalkylarylsiloxanes are particularly chosen from linear and/or branched polydimethyl/methylphenylsiloxanes and polydimethyl/diphenylsiloxanes with a viscosity ranging from $1\times10^{-5}$ to $5\times10^{-2}$ m$^2$/s at 25° C.

Mention may be made, among these polyalkylarylsiloxanes, by way of example, of the products sold under the following names:
- the Silbione® oils of the 70 641 series from Rhodia;
- the oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

Mention may be made, among the organomodified silicones, of polyorganosiloxanes comprising:
- substituted or unsubstituted amino groups, such as the products sold under the name GP 4 Silicone Fluid and GP 7100 by the company Genesee or the products sold under the names Q2 8220 and Dow Corning 929 or 939 by the company Dow Corning. The substituted amino groups are, in particular, $C_1$-$C_4$ aminoalkyl groups;
- alkoxylated groups, such as the product sold under the name Silicone Copolymer F-755 by SWS Silicones, and Abil Wax® 2428, 2434 and 2440 by the company Goldschmidt.

More particularly, the fatty substances are chosen from compounds that are liquid or pasty at room temperature (25° C.) and at atmospheric pressure.

Preferably, the fatty substance is a compound that is liquid at a temperature of 25° C. and at atmospheric pressure.

The fatty substances are advantageously chosen from $C_6$-$C_{16}$ alkanes, non-silicone oils of plant, mineral or synthetic origin, fatty alcohols, fatty acid and/or fatty alcohol esters, or mixtures thereof.

Preferably, the fatty substance is chosen from liquid petroleum jelly, $C_6$-$C_{16}$ alkanes, polydecenes, liquid fatty acid and/or fatty alcohol esters, liquid fatty alcohols, or mixtures thereof.

The composition according to the invention, free of oxidizing agent other than atmospheric oxygen, preferably comprises at least 10% by weight, even more preferentially at least 15% by weight, even more advantageously at least 30% by weight, and up to 70% by weight, relative to the total weight of the composition.

In accordance with a particularly advantageous embodiment, the composition according to the invention, after mixing with the oxidizing composition, comprises at least 10% by weight, relative to the total weight of the composition, preferably at least 15% by weight and even more advantageously at least 30% by weight, relative to the total weight of the composition, and up to 70% by weight relative to the total weight of the composition.

Nonionic Guar Gum

The composition according to the invention comprises at least one nonionic guar gum.

The term "nonionic guar gum" means unmodified nonionic guar gums and modified nonionic guar gums.

The unmodified nonionic guar gums are, for example, the products sold under the name Vidogum GH 175 by the company Unipectine and under the names Meypro-Guar 50 and Jaguar C by the company Rhodia Chimie.

The modified nonionic guar gums are especially modified with $C_1$-$C_6$ hydroxyalkyl groups.

Among the hydroxyalkyl groups that may be mentioned, for example, are hydroxymethyl, hydroxyethyl, hydroxypropyl and hydroxybutyl groups.

These hydroxyalkylated guar gums are well known in the prior art and can be prepared, for example, by reacting corresponding alkene oxides such as, for example, propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, preferably ranges from 0.4 to 1.2.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Rhodia Chimie or under the name Galactasol 4H4FD2 by the company Aqualon.

Also suitable are nonionic guar gums modified with hydroxyalkyl groups, more especially hydroxypropyl groups, modified with groups comprising at least one $C_6$-$C_{30}$ fatty chain. By way of example of such compounds, mention may be made, inter alia, of the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhône-Poulenc.

More particularly, the content of nonionic guar gum(s) ranges from 0.001% to 10% by weight, preferably from 0.01% to 5% by weight, better still from 0.1% to 5% by weight and even better still from 1% to 5% by weight relative to the total weight of the composition.

Preferably, the nonionic guar gum(s)/amphoteric or zwitterionic surfactant(s) weight ratio ranges from 0.2 to 5 and better still from 0.5 to 2.

Alkaline Agent

The composition according to the invention advantageously comprises at least one alkaline agent.

This agent may be chosen from mineral or organic or hybrid alkaline agents, or mixtures thereof.

The mineral alkaline agent(s) are preferably chosen from aqueous ammonia, alkali carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a pKb at 25° C. of less than 12, preferably less than 10 and even more advantageously less than 6. It should be noted that it is the pKb corresponding to the function of highest basicity.

Mention may be made, as hybrid compounds, of the salts of the abovementioned amines with acids, such as carbonic acid or hydrochloric acid.

The organic alkaline agent(s) are chosen, for example, from alkanolamines, oxyethylenated and/or oxypropylenated ethylenediamines, amino acids and the compounds having the formula below:

$$\begin{array}{c} Rx \\ \diagdown \\ N-W-N \\ \diagup \\ Ry \end{array} \begin{array}{c} Rz \\ \diagup \\ \diagdown \\ Rt \end{array}$$

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising from one to three identical or different $C_1$-$C_4$ hydroxyalkyl radicals are in particular suitable for implementing the invention.

Among compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function chosen more particularly from carboxylic acid, phosphonic acid or phosphoric acid functions. The amino acids may be in neutral or ionic form.

As amino acids that can be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, threonine, tryptophan, tyrosine and valine.

Advantageously, the amino acids are basic amino acids comprising an additional amine function optionally included in a ring or in a ureido function.

Such basic amino acids are preferably chosen from those corresponding to the formula below:

$$R-CH_2-CH\begin{array}{c} NH_2 \\ \diagup \\ \diagdown \\ CO_2H \end{array}$$

in which R denotes a group chosen from:

$$\begin{array}{c} \underset{NH}{\underbrace{\phantom{XXX}}}\!\!\diagdown\!\!N \end{array} \quad -(CH_2)_3NH_2 \quad -(CH_2)_2NH_2$$

$$-(CH_2)_2NH-\underset{\underset{NH}{\parallel}}{C}-NH_2 \quad -(CH_2)_2NHCONH_2$$

The compounds corresponding to the formula above are histidine, lysine, arginine, ornithine and citrulline.

The organic amine may also be chosen from organic amines of heterocyclic type. Besides histidine that has already been mentioned in the amino acids, mention may be made in particular of pyridine, piperidine, imidazole, triazole, tetrazole and benzimidazole.

The organic amine can also be chosen from amino acid dipeptides. As amino acid dipeptides that may be used in the present invention, mention may be made especially of carnosine, anserine and balenine.

The organic amine is chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid and 4-guanidinobutyric acid.

As hybrid compounds, mention may be made in particular of guanidine carbonate or monoethanolamine hydrochloride.

More particularly, the dye composition used in the process of the invention contains, as alkaline agent, aqueous ammonia and/or at least one alkanolamine and/or at least one basic amino acid, more advantageously aqueous ammonia and/or at least one alkanolamine. Preferably, the alkaline agent is chosen from aqueous ammonia and monoethanolamine, or mixtures thereof. Even more preferentially, the alkaline agent is an alkanolamine and better still the alkaline agent is monoethanolamine.

Advantageously, the composition has a content of alkaline agent(s), and preferably of organic amine(s), ranging from 0.01% to 30% by weight, preferably from 0.1% to 20% by weight and better still from 1% to 10% by weight, relative to the weight of the said dye composition. It should be noted that this content is expressed as $NH_3$ when the alkaline agent is aqueous ammonia.

Sulfur Compounds

In accordance with a particularly advantageous variant of the invention, the composition comprises at least one aminoalkane sulfonic, sulfonothioic or sulfinic acid, and also salts thereof or amide derivatives thereof or functional analogues thereof.

Preferably, such compounds are chosen from the compounds corresponding to formula (A) or (B) below:

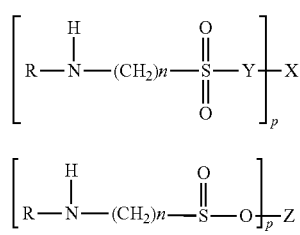

in which:
R denotes hydrogen;
Y denotes S or O;
X denotes hydrogen, a cation $M^{p+}$ of valency p, or an organic amine;
Z denotes hydrogen, a cation $M^{p+}$ of valency p, or an organic amine;
n is an integer greater than or equal to 2;
p is an integer greater than or equal to 1.
Preferentially:
R denotes hydrogen or a linear $C_1$-$C_4$ alkyl radical and more preferentially methyl;
p is 1 or 2;
n is 2 or 3;
X denotes hydrogen or a cation $M^{p+}$ chosen from alkali metals (K+, Na+), alkaline-earth metals ($Mg^{2+}$, $Ca^{2+}$) and the ammonium ion;
Z denotes hydrogen or a cation $M^{p+}$ chosen from alkali metals (K+, Na+), alkaline-earth metals ($Mg^{2+}$, $Ca^{2+}$) and the ammonium ion.

Among the compounds of formula (A), mention may be made more particularly, alone or as mixtures, of:
taurine or 2-aminoethanesulfonic acid;
thiotaurine or 2-aminoethanesulfonothioic acid;
homotaurine or 2-aminopropanesulfonic acid;
salts thereof such as:
potassium taurate, in particular potassium taurate as a mixture with lauric acid (INCI name: Potassium Taurate Laurate) such as the commercial product L-TK sold by the company NOF Corporation;
sodium taurate, in particular as a mixture with lauric acid, such as the commercial product L-T2 sold by the company NOF Corporation.

Among the compounds of formula (B), mention may be made more particularly of hypotaurine or 2-aminoethanesulfinic acid, and salts thereof.

The aminoalkane sulfonic, sulfonothioic or sulfinic acid compounds, and also the salts thereof or amide derivatives thereof may also be chosen from functional analogues of taurine such as those described in the article *Taurine analogues, a new class of therapeutics: retrospect and prospects*, Gupta R. C., Win T., Bittner S. Curr. Med. Chem.

Taurine, homotaurine or hypotaurine or salts thereof will be chosen more particularly, and even more particularly taurine and salts thereof.

Preferentially, the aminoalkane sulfonic, sulfonothioic or sulfinic acid compound(s), and salts thereof, amide derivatives thereof or functional analogues thereof in accordance with the invention are present in the composition in concentrations ranging from 0.005% to 1% by weight and preferably from 0.005% to 0.5% by weight relative to the total weight of the composition.

Compound of Ceramide Type

In accordance with one variant of the invention, the composition comprises at least one compound of ceramide type.

More particularly, the compound of ceramide type is of formula (C):

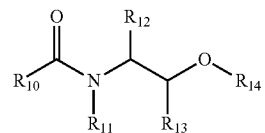

in which formula (C):
$R_{10}$ denotes:
i) a linear or branched, saturated or unsaturated $C_1$-$C_{50}$, preferably $C_5$-$C_{50}$, hydrocarbon-based radical, this radical possibly being substituted with one or more hydroxyl groups optionally esterified with an acid $R_{15}$COOH, with $R_{15}$ being a saturated or unsaturated, linear or branched, optionally mono- or polyhydroxylated $C_1$-$C_{35}$ hydrocarbon-based radical, the hydroxyl group(s) of the radical $R_{15}$ possibly being esterified with a saturated or unsaturated, linear or branched, optionally mono- or polyhydroxylated $C_1$-$C_{35}$ fatty acid;
ii) a radical R"—(NR—CO)$_q$—R', with R denoting a hydrogen atom or a mono- or polyhydroxylated, preferentially monohydroxylated, $C_1$-$C_{20}$ hydrocarbon-based radical, R' and R" are hydrocarbon-based radicals in which the sum of the carbon atoms is between 9 and 30, R' being a divalent radical and q denotes 0 or 1; or
iii) a radical $R_{16}$—O—CO—(CH$_2$)$_p$, $R_{16}$ denotes a $C_1$-$C_{20}$ hydrocarbon-based radical and p is an integer from 1 to 12 inclusive;
$R_{11}$ is chosen from a hydrogen atom, a radical of saccharide type, in particular a (glycosyl)$_n$, (galactosyl)$_m$ or sulfogalactosyl radical, a sulfate or phosphate residue, a phosphorylethylamine radical and a phosphorylethylammonium radical, in which n is an integer between 1 and 4 inclusive, and m is an integer between 1 and 8 inclusive;
$R_{12}$ denotes a saturated or unsaturated, optionally hydroxylated $C_1$-$C_{33}$ hydrocarbon-based radical, the hydroxyl group(s) possibly being esterified with a mineral acid or an acid $R_{15}$COOH, $R_{15}$ having the same meanings as previously, the hydroxyl group(s) possibly being etherified with a (glycosyl)$_n$, (galactosyl)$_m$, sulfogalactosyl, phosphorylethylamine or phosphorylethylammonium radical, $R_{12}$ also possibly being substituted with one or more $C_1$-$C_{14}$ alkyl radicals;
preferably, $R_{12}$ denotes a $C_{15}$-$C_{26}$ α-hydroxyalkyl radical, the hydroxyl group being optionally esterified with a $C_{16}$-$C_{30}$ α-hydroxy acid;

$R_{13}$ denotes a hydrogen atom, a saturated or unsaturated, linear or branched, optionally hydroxylated $C_3$-$C_{50}$ non-alkoxylated hydrocarbon-based radical, such as a methyl or ethyl radical, or a radical $R_{16}$—O—CO—$(CH_2)_p$, $R_{14}$ denotes a $C_1$-$C_{20}$ hydrocarbon-based radical, p is an integer ranging from 1 to 12;

$R_{14}$ denotes a hydrogen atom or a saturated or unsaturated, linear or branched, optionally mono- or polyhydroxylated $C_1$-$C_{30}$ hydrocarbon-based radical, the hydroxyl group(s) possibly being etherified with a (glycosyl)$_n$, (galactosyl)$_m$, sulfogalactosyl, phosphorylethylamine or phosphorylethylammonium radical.

Preferably, the compound of ceramide type is of formula (C) in which $R_{10}$ denotes a $C_{12}$-$C_{20}$ alkenyl chain comprising one or two double bonds; $R_{11}$ denotes a hydrogen atom; $R_{12}$ denotes an optionally hydroxylated linear $C_{11}$-$C_{17}$ radical; $R_{13}$ represents a $C_{10}$-$C_{20}$ alkyl group and $R_{14}$ represents a hydrogen atom.

More particularly, the compound of ceramide type is chosen from:
2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol and in particular N-stearoylphytosphingosine,
2-N-palmitoylaminohexadecane-1,3-diol,
or a mixture of these compounds.

When the composition comprises at least one compound of ceramide type, its content is between 0.005% and 1% by weight and preferably between 0.005% and 0.1% by weight relative to the weight of the composition.

Oxidizing Agent

The composition according to the invention may also comprise at least one oxidizing agent other than atmospheric oxygen.

In particular, the oxidizing agent(s) suitable for use in the present invention are chosen, for example, from hydrogen peroxide, urea peroxide, alkali metal bromates or ferricyanides, peroxygenated salts, for instance persulfates, perborates, peracids and precursors thereof and percarbonates of alkali metals or alkaline-earth metals. Advantageously, the oxidizing agent is hydrogen peroxide.

Additives

The composition may also contain various adjuvants conventionally used in compositions for dyeing or lightening the hair, such as anionic, cationic, nonionic or amphoteric polymers, or mixtures thereof; cationic surfactants; antioxidants; penetrants; sequestrants; fragrances; dispersants; film-forming agents; ceramides; preserving agents; opacifiers.

The above adjuvants are generally present in an amount, for each of them, of between 0.01% and 20% by weight relative to the weight of the composition.

The composition according to the invention may comprise water and/or one or more organic solvents.

Examples of organic solvents that may be mentioned include linear or branched and preferably saturated monoalcohols or diols, comprising 2 to 10 carbon atoms, such as ethyl alcohol, isopropyl alcohol, hexylene glycol (2-methyl-2,4-pentanediol), neopentyl glycol and 3-methyl-1,5-pentanediol, butylene glycol, dipropylene glycol and propylene glycol; aromatic alcohols such as benzyl alcohol or phenylethyl alcohol; polyols containing more than two hydroxyl functions, such as glycerol; polyol ethers, for instance ethylene glycol monomethyl, monoethyl and monobutyl ethers, propylene glycol or ethers thereof, for instance propylene glycol monomethyl ether; and also diethylene glycol alkyl ethers, especially $C_1$-$C_4$ alkyl ethers, for instance diethylene glycol monoethyl ether or monobutyl ether, alone or as a mixture.

The organic solvents, when they are present, generally represent between 1% and 40% by weight relative to the total weight of the dye composition, and preferably between 5% and 30% by weight relative to the total weight of the dye composition.

The composition is preferably aqueous. In this case, it preferably comprises from 30% to 95% by weight of water, better still from 40% to 90% by weight of water and even better still from 50% to 85% by weight of water relative to the total weight of the composition.

The pH of the composition according to the invention, if it is aqueous, generally ranges from 6 to 11 and preferentially from 8.5 to 11.

It may be adjusted to the desired value by means of acidifying or basifying agents usually used in the dyeing of keratin fibres.

Dyeing Process

The dyeing process according to the invention consists in applying to human keratin fibres a composition preferably in foam form obtained by mixing a dye composition as described previously, free of oxidizing agent other than atmospheric oxygen, with a composition comprising at least one oxidizing agent other than atmospheric oxygen.

In a preferred variant of the invention, the composition after mixing is thus, when applied to the fibres, in the form of a foam.

The composition in foam form is formed from a mixture of air or an inert gas with the composition described previously.

According to a particularly preferred embodiment, the composition according to the invention is in the form of a temporary foam produced just before use.

According to this embodiment, the composition may be packaged in a foam dispenser.

It may either be a case of "aerosol" products dispensed from a pressurized container by means of a propellant gas and thus forming a foam at the moment when they are dispensed.

It may also be a case of products dispensed from a container which is closed by means of a dispensing head, the passage of the composition through the dispensing head transforming the composition into foam at the very latest at the outlet orifice of such a head, this being achieved by pressure exerted by hands on the container.

It may also be a case of products dispensed from a container which is closed by means of a dispensing head, the passage of the composition through the dispensing head transforming the composition into foam at the very latest at the outlet orifice of such a head, this being achieved by pressure exerted by hands on the container.

Finally, the foam may be obtained by shaking the mixture of the composition according to the invention with an oxidizing composition in a shaker.

According to a first variant, the dispenser may be an aerosol, containing, besides the base composition, which is generally divided into two parts, one with the oxidizing agent(s) and the other with the dye precursor(s), a propellent gas. In such a configuration the two portions are generally stored separately, each in a pressurized container. Thus, the propellent gases selected in each of the containers may be suitable for the portion contained.

The propellent gas that may be used may be chosen from carbon dioxide, nitrogen, nitrogen oxide, dimethyl ether, volatile hydrocarbons such as butane, isobutane, propane, pentane, and mixtures thereof.

In practice, for this variant, use will be made of either aerosol packaging with a single container that internally contains two pouches, or a double aerosol that therefore contains two containers. In both cases, the dispensing head is such that what is sprayed in foam form is the composition according to the invention, that is to say the mixture of the composition with the oxidizing agent(s) and the composition with the oxidation dye precursor(s).

According to another embodiment, the composition may be in a foam dispenser of the "pump bottle" type. These dispensers comprise a dispensing head for delivering the composition, a pump and a dip tube for transferring the composition from the container into the head in order to deliver the product. The foam is formed by forcing the composition to pass through a material comprising a porous substance such as a sintered material, a filtering grid made of plastic or of metal, or similar structures.

Such dispensers are well known to those skilled in the art and are described in patents: U.S. Pat. No. 3,709,437 (Wright), U.S. Pat. No. 3,937,364 (Wright), U.S. Pat. No. 4,022,351 (Wright), U.S. Pat. No. 4,147,306 (Bennett), U.S. Pat. No. 4,184,615 (Wright), U.S. Pat. No. 4,598,862 (Rice), U.S. Pat. No. 4,615,467 (Grogan et al.), and U.S. Pat. No. 5,364,031 (Tamiguchi et al.).

According to another embodiment, the composition may be in a foam dispenser comprising a dispensing head for delivering the composition, and a dip tube for transferring the composition from the container to the head; the passage of the composition to the dispensing head being performed by exerting a pressure on the flexible walls of the container (squeeze bottle).

In practice, for these last two variants, the oxidizing composition is conditioned in a first container equipped with a stopper, and the dye composition is conditioned in a second container, separate from the first, and also closed by means of a closing member. The closing member may be a pump-dispensing mechanism. The ready-to-use composition is then formed by mixing, before use, a composition with the oxidizing agent(s) and a composition according to the invention with the oxidation dye precursor(s). To this end, to limit the number of containers provided, one from among the first and second container defines an internal volume that is sufficient to receive therein all of the two compositions. The mixture of the compositions may be homogenized by closing this container and by shaking the container. The closure of the container is advantageously carried out directly with the dispensing head. This dispensing head may comprise a mechanical pump held in a ring intended for mounting by snap-fitting or screwing onto the neck of the container containing the mixture. The pump comprises a pump body connected to a dip tube to enable all of the mixture to be dispensed. The pump also comprises a push button for activation of the pump body, such that, on each activation, a dose of composition is sucked up into the dip tube and ejected in foam form out of the dispensing orifice of the head.

If the container does not comprise a pump, the dispensing head is connected to a dip tube to enable dispensing of all of the mixture.

In these two variants, the containers are preferably made of a thermoplastic material and are obtained by extrusion blow moulding or injection blow moulding processes. In particular, the container intended for packaging the composition with the oxidation dye precursor(s) is made of a material comprising a non-zero proportion of EVOH.

If the container comprises a pump, it is, for example, the standard "F2-L9" model offered by the company Rexam.

According to this preferred embodiment, a subject of the invention is a non-aerosol device comprising the ready-to-use composition derived from the mixing of the composition of the invention with an oxidizing composition.

The dyeing process according to the invention consists in applying to wet or dry human keratin fibres a composition resulting from the mixing of a composition as described previously, free of oxidizing agent other than air, with a composition comprising at least one oxidizing agent.

The composition is left in place for a time sufficient to develop the desired coloration.

The dyeing process is generally performed at room temperature (between 15 and 25° C.) and up to temperatures that may be as high as 60° C. to 80° C.

After a leave-on time of from one minute to one hour and preferably from 5 minutes to 30 minutes, the keratin fibres are rinsed with water, optionally washed with a shampoo and then rinsed with water.

The examples that follow serve to illustrate the invention without, however, being limiting in nature.

EXAMPLE 1

The following compositions are prepared (the amounts are expressed in g % of active material):

Composition 1:

| Ingredients | Content |
| --- | --- |
| Resorcinol | 0.5 |
| Ethanolamine | 2.824 |
| Sodium laureth sulfate containing 2.2 OE | 1.75 |
| Hydroxypropyl guar | 2.25 |
| Ascorbic acid | 0.5 |
| N,N-Bis(2-hydroxyethyl)-p-phenylenediamine sulfate | 0.073 |
| m-Aminophenol | 0.18 |
| EDTA | 0.2 |
| 2-Methylresorcinol | 0.1 |
| PEG-40 hydrogenated castor oil | 1 |
| 2,4-Diaminophenoxyethanol hydrochloride | 0.019 |
| Cocoylbetaine | 3 |
| Sodium chloride | 0.65 |
| Sodium metabisulfite | 0.5 |
| Mineral oil (liquid paraffin) | 60 |
| 2,5-Toluenediamine | 0.6732 |
| Water | qs 100 |

Composition 2:

| Ingredients | Content |
| --- | --- |
| Caprylyl/capryl glucoside | 1.8 |
| Tetrasodium etidronate | 0.06 |
| Sodium salicylate | 0.035 |
| Glycerol | 4 |
| Hydrogen peroxide | 6 |
| Tetrasodium pyrophosphate | 0.04 |

-continued

| Ingredients | Content |
| --- | --- |
| Phosphoric acid | qs pH 2.2 |
| Water | qs |

Application Method:

The two compositions are mixed together at the time of use, for example in a shaker, in the following proportions: 9 g of composition 1 with 12 g of composition 2.

The foam thus obtained is creamy. It is applied to locks of grey hair containing 90% white hairs, in a proportion of 10 g of mixture per 1 g of hair, for 30 minutes at room temperature (20° C.).

The hair is then rinsed, washed with a standard shampoo and dried.

A strong light chestnut colouring is obtained.

EXAMPLE 2

The following compositions are prepared (the amounts are expressed in g % of active material):
Composition 1:

| Ingredients | Content |
| --- | --- |
| Resorcinol | 0.5 |
| Ethanolamine | 2.824 |
| Sodium laureth sulfate containing 2.2 OE | 1.75 |
| Hydroxypropyl guar | 2.25 |
| Ascorbic acid | 0.5 |
| N,N-Bis(2-hydroxyethyl)-p-phenylenediamine sulfate | 0.073 |
| m-Aminophenol | 0.18 |
| EDTA | 0.2 |
| 2-Methylresorcinol | 0.1 |
| PEG-40 hydrogenated castor oil | 1 |
| 2,4-Diaminophenoxyethanol hydrochloride | 0.019 |
| Cocoylbetaine | 3 |
| Sodium chloride | 0.65 |
| Sodium metabisulfite | 0.5 |
| Mineral oil | 60 |
| Taurine | 0.01 |
| 2,5-Toluenediamine | 0.6732 |
| Water | qs 100% |

Composition 2:

| Ingredients | Content |
| --- | --- |
| Caprylyl/capryl glucoside | 1.8 |
| Tetrasodium etidronate | 0.06 |
| Sodium salicylate | 0.035 |
| Glycerol | 4 |
| Hydrogen peroxide | 6 |
| Tetrasodium pyrophosphate | 0.04 |
| Phosphoric acid | qs pH 2.2 |
| Water | qs 100% |

Application Method:

The two compositions are mixed together at the time of use in the following proportions: 9 g of composition 1+12 g of composition 2 and are applied to locks of grey hair containing 90% white hairs, in a proportion of 10 g of mixture per 1 g of hair, for 30 minutes.

The hair is then rinsed, washed with a standard shampoo and dried.

A light chestnut colouring is obtained.

EXAMPLE 3

The following compositions are prepared (the amounts are expressed in g % of active material):
Composition 1:

| Ingredients | Content |
| --- | --- |
| Resorcinol | 0.5 |
| Ethanolamine | 2.824 |
| Sodium laureth sulfate containing 2.2 OE | 1.75 |
| Hydroxypropyl guar | 2.25 |
| Ascorbic acid | 0.5 |
| N,N-Bis(2-hydroxyethyl)-p-phenylenediamine sulfate | 0.073 |
| m-Aminophenol | 0.18 |
| EDTA | 0.2 |
| 2-Methylresorcinol | 0.1 |
| PEG-40 hydrogenated castor oil | 1 |
| 2,4-Diaminophenoxyethanol hydrochloride | 0.019 |
| Cocoylbetaine | 3 |
| Sodium chloride | 0.65 |
| Sodium metabisulfite | 0.5 |
| Mineral oil | 60 |
| 2-Oleamido-1,3-octadecanediol | 0.01 |
| 2,5-Toluenediamine | 0.6732 |
| Water | qs 100% |

Composition 2:

| Ingredients | Content |
| --- | --- |
| Tetrasodium etidronate | 0.06 |
| Sodium salicylate | 0.035 |
| Glycerol | 4 |
| Hydrogen peroxide | 6 |
| Tetrasodium pyrophosphate | 0.04 |
| Phosphoric acid | qs pH 2.2 |
| Water | qs 100% |

Application Method:

The two compositions are mixed together at the time of use in the following proportions: 9 g of composition 1+12 g of composition 2 and are applied to locks of grey hair containing 90% white hairs, in a proportion of 10 g of mixture per 1 g of hair, for 30 minutes.

The hair is then rinsed, washed with a standard shampoo and dried.

A light chestnut colouring is obtained.

EXAMPLE 4

The following compositions are prepared (the amounts are expressed in g % of active material):
Composition 1 and 1':

| Ingredients | 1 | 1' |
| --- | --- | --- |
| p-Aminophenol | 0.18886 | 0.46 |
| EDTA | 0.2 | 0.2 |
| Ethanolamine | 5.16 | 5.16 |
| 1-Hydroxyethyl-4,5-diaminopyrazole sulfate | 1.58 | |
| 2,3-Diamino-6,7-dihydro-1H,5H-pyrazolo(1,2-a)pyrazol-1-one dimethanesulfonate | | 0.8 |
| 4-Amino-2-hydroxytoluene | 1.3 | 0.81 |
| Sodium laureth sulfate containing 2.2 OE | 1.75 | 1.75 |
| Hydroxypropyl guar | 2.25 | 2.25 |
| Ascorbic acid | 0.5 | 0.5 |
| PEG-40 hydrogenated castor oil | 1 | 1 |
| Cocoylbetaine | 3 | 3 |

-continued

| Ingredients | 1 | 1' |
|---|---|---|
| Sodium chloride | 0.65 | 0.65 |
| Sodium metabisulfite | 0.5 | 0.5 |
| Mineral oil | 60 | 60 |
| 5-Amino-6-chloro-o-cresol | 0.28 | |
| 1-Methyl-2-hydroxy-4-β-hydroxyethylaminobenzene | | 0.4 |
| 2,5-Toluenediamine | 0.4653 | 0.26 |
| Water | qs 100% | |

Composition 2:

| Ingredients | Content |
|---|---|
| Caprylyl/capryl glucoside | 1.8 |
| Tetrasodium etidronate | 0.06 |
| Sodium salicylate | 0.035 |
| Glycerol | 4 |
| Hydrogen peroxide | 6 |
| Tetrasodium pyrophosphate | 0.04 |
| Phosphoric acid | qs pH 2.2 |
| Water | qs 100% |

Application Method:

The two compositions 1 and 1' are mixed at the time of use with composition 2 in the following proportions: 9 g of composition 1 or 1' with 12 g of composition 2. The mixtures are then applied to locks of grey hair containing 90% white hairs, in a proportion of 10 g of mixture per 1 g of hair, for 30 minutes.

The hair is then rinsed, washed with a standard shampoo and dried.

A deep red light chestnut colouring is obtained with the mixture of composition 1 and of composition 2, and a coppery-red light chestnut colouring is obtained with the mixture of composition 1' and of composition 2.

The invention claimed is:

1. A composition for dyeing human keratin fibers comprising:
   at least one oxidation dye precursor;
   at least one amphoteric or zwitterionic surfactant;
   at least one second surfactant chosen from nonionic surfactants, anionic surfactants, or mixtures thereof;
   at least one fatty substance other than ceramides chosen from liquid petroleum jelly, C6-C16 alkanes, polydecenes, or esters of fatty acids or of fatty alcohols, which are liquid, or mixtures thereof; and
   at least one nonionic guar gum chosen from modified nonionic guar gums modified with C1-C6 hydroxyalkyl groups.

2. The composition according to claim 1, wherein the at least one oxidation dye precursor is chosen from oxidation bases.

3. The composition according to claim 1, wherein the at least one oxidation dye precursor is chosen from diaminodiazacyclopentene derivatives.

4. The composition according to claim 1, wherein the at least one oxidation dye precursor is chosen from diaminopyrazolone compounds of formula (I), and salts thereof:

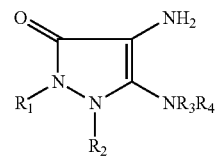

wherein:
$R_1$, $R_2$, $R_3$ and $R_4$, which may be identical or different, are chosen, independently of each other, from:
a hydrogen atom;
a linear or branched $C_1$-$C_{10}$, optionally substituted with one or more groups chosen from $OR_5$, $NR_6R_7$ and carboxy groups, sulfonic, carboxamido $CONR_6R_7$ and sulfonamido $SO_2NR_6R_7$ groups, aliphatic heterocycles, aryls optionally substituted with one or more group(s) chosen from $C_1$-$C_4$ alkyl, hydroxyl, $C_1$-$C_2$ alkoxy, amino and (di)($C_i$-$C_2$)alkylamino groups;
an aryl group optionally substituted with one or more group(s) chosen from $C_1$-$C_4$ alkyl, hydroxyl, $C_1$-$C_2$ alkoxy, amino and (di)($C_2$-$C_2$)alkylamino groups; or
a 5- or 6-membered heteroaryl group, optionally substituted with one or more group(s) chosen from $C_1$-$C_4$ alkyl and $C_1$-$C_2$ alkoxy groups;
$R_5$, $R_6$ and $R_7$, which may be identical or different, are chosen from:
a hydrogen atom;
a linear or branched $C_1$-$C_4$ alkyl group, optionally substituted with one or more group(s) chosen from hydroxyl, $C_1$-$C_2$ alkoxy, carboxamido $CONR_8R_9$, and sulfonyl $SO_2R_8$ groups, aryl optionally substituted with a $C_1$-$C_4$ alkyl, hydroxyl, $C_1$-$C_2$ alkoxy, amino or (di)($C_i$-$C_2$)alkylamino group;
an aryl group optionally substituted with one or more group(s) chosen from $C_1$-$C_4$ alkyl, hydroxyl, $C_1$-$C_2$ alkoxy, amino and (di)($C_i$-$C_2$)alkylamino groups;
a carboxamido $CONR_8R_9$ group; or
a sulfonyl $SO_2R_8$ group;
$R_8$ and $R_9$, which may be identical or different, are chosen from:
a hydrogen atom; or
a linear or branched $C_1$-$C_4$ alkyl group, optionally substituted with one or more group(s) chosen from hydroxyl and $C_1$-$C_2$ alkoxy groups;
$R_1$ and $R_2$, on the one hand, and $R_3$ and $R_4$, on the other hand, may also form, together with the nitrogen atom(s) to which they are attached, a saturated or unsaturated 5- to 7-membered heterocycle, which is optionally substituted or N-substituted with one or more group(s) chosen from halogen atoms, amino, (di)($C_1$-$C_4$)alkylamino, (di)hydroxy($C_1$-$C_2$)alkylamino, hydroxyl, carboxy, carboxamido, (di)($C_1$-$C_2$)alkylcarboxamido and $C_1$-$C_2$ alkoxy groups and $C_1$-$C_4$ alkyl groups optionally substituted with one or more groups chosen from hydroxyl, amino, (di)alkylamino, alkoxy, carboxy and sulfonyl groups; the said heterocycles formed by $R_1$ and $R_2$, on the one hand, and $R_3$ and $R_4$, on the other hand, with the nitrogen atom(s) to which they are attached, possibly being identical or different, and the ring members forming the said heterocycles possibly being chosen from carbon, nitrogen and oxygen atoms.

5. The composition according to claim 1, wherein the at least one oxidation dye precursor is chosen 2,3-diamino-6,7-dihydro-1H, 5H-pyrazolo[1,2-a]pyrazol-1-one and salts thereof.

6. The composition according to claim 1, wherein the at least one oxidation dye precursor is chosen diaminopyrazole compounds of formula (II), and salts thereof:

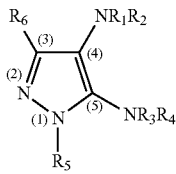
(II)

wherein:
$R_1$, $R_2$, $R_3$, $R_4$ and $R_5$, which may be identical or different, are chosen from:
a hydrogen atom;
a $C_1$-$C_6$ alkyl radical which is unsubstituted or substituted with at least one substituent chosen from OR, NHR, NRR', SR, SOR, $SO_2R$, COR, COOH, $CONH_2$, CONHR, CONRR', $PO(OH)_2$, SH, $SO_3X$, a non-cationic heterocycle, CI, Br or I, X denoting a hydrogen atom, Na, K or $NH_4$, and R and R', which may be identical or different, representing a $C_1$-$C_4$ alkyl or alkenyl;
a $C_2$-$C_4$ hydroxyalkyl radical;
a $C_2$-$C_4$ aminoalkyl radical; a phenyl radical;
a phenyl radical substituted with a halogen atom or a $C_1$-$C_4$ alkyl, $C_1$-$C_4$ alkoxy, nitro, trifluoromethyl, amino or $C_1$-$C_4$ alkylamino radical;
a benzyl radical; a benzyl radical substituted with a halogen atom or with a $C_1$-$C_4$ alkyl, $C_1$-$C_4$ alkoxy, methylenedioxy or amino radical;
a radical

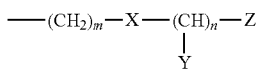

wherein:
m and n are equal to integers, which may be identical or different, range from 0 to 3,
X is chosen from an oxygen atom or an NH group,
Y is chosen from a hydrogen atom or a $C_1$-$C_4$ alkyl radical, and
Z is:
a methyl radical when n is equal to 0, or
Z is chosen from a $C_1$-$C_4$ alkyl radical or a group OR or NR"R'"when n is greater than or equal to 1, R as defined above, and R" and R'", which may be identical or different, are chosen from a hydrogen atom or a $C_1$-$C_4$ alkyl radical;
$R_6$ is chosen from a $C_1$-$C_6$alkyl radical; a $C_1$-$C_4$ hydroxyalkyl radical; a $C_1$-$C_4$ aminoalkyl radical; a ($C_1$-$C_4$) alkylamino($C_1$-$C_4$)alkyl radical; a di($C_1$-$C_4$)alkylamino($C_1$-$C_4$)alkyl radical; a hydroxy($C_1$-$C_4$) alkylamino($C_1$-$C_4$)alkyl radical; a ($C_1$-$C_4$) alkoxymethyl radical; a phenyl radical; a phenyl radical substituted with a halogen atom or with a ($C_1$-$C_4$)alkyl, ($C_1$-$C_4$)alkoxy, nitro, trifluoromethyl, amino or ($C_1$-$C_4$) alkylamino radical; a benzyl radical; a benzyl radical substituted with a halogen atom or with a ($C_1$-$C_4$)alkyl, ($C_1$-$C_4$) alkoxy, nitro, trifluoromethyl, amino or ($C_1$-$C_4$)alkylamino radical; a heterocycle chosen from thiophene, furan and pyridine, or else a —$(CH_2)_p$—O—$(CH_2)_q$—OR" radical, wherein p and q are integers, which may be identical or different, range from 1 to 3, and R" as defined above;
wherein at least one of the radicals $R_1$, $R_2$, $R_3$ and $R_4$ represents a hydrogen atom.

7. The composition according to claim 1, wherein the at least one oxidation dye precursor is chosen from 4,5-diamino-1-(2-hydroxyethyl)-1H-pyrazole and salts thereof.

8. The composition according to claim 1, wherein the composition comprises at least one oxidation dye precursor chosen from couplers.

9. The composition according claim 1, wherein the at least one amphoteric or zwitterionic surfactant is chosen from derivatives of optionally quaternized aliphatic secondary or tertiary amines, where the aliphatic group of the derivative is a linear or branched chain comprising from 8 to 22 carbon atoms, the said amine derivatives comprising at least one anionic group.

10. The composition according to claim 9, wherein the at least one amphoteric or zwitterionic surfactant is chosen from:
($C_8$-$C_{20}$)alkylbetaines,
($C_8$-$C_{20}$)alkylsulfobetaines,
($C_8$-$C_{20}$)alkylamido($C_3$-$C_8$)alkylbetaines,
($C_8$-$C_{20}$)alkylamido($C_6$-$C_8$)alkylsulfobetaines,
the compounds of formula (B1):

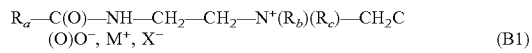
(B1)

wherein:
$R_a$ is chosen from a $C_{10}$-$C_{30}$ alkyl or alkenyl group derived from an acid $R_a$COOH, heptyl, nonyl or undecyl group;
$R_b$ is a β-hydroxyethyl group; and
$R_c$ is a carboxymethyl group;
$M^+$is chosen from a cationic counterion derived from an alkali metal or alkaline-earth metal or an ammonium ion or an ion derived from an organic amine; and
$X^-$is chosen from an organic or mineral anionic counterion chosen from halides, acetates, phosphates, nitrates, ($C_1$-$C_4$)alkyl sulfates, ($C_1$-$C_4$) alkyl- or ($C_1$-$C_4$)alkylarylsulfonates, or mixtures thereof;
or alternatively $M^+$and $X^-$are absent;
the compounds of formula (B2) below:

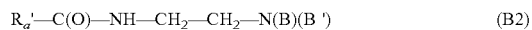
(B2)

wherein:
B is the group —$CH_2$—$CH_2$—O—X';
B' is the group —$(CH_2)_z$Y', with z equal to an integer 1 or 2;
X' is chosen from the groups —$CH_2$—C(O)OH, —$CH_2$—C(O)OZ', —$CH_2$—$CH_2$—C(O)OH, —$CH_2$—$CH_2$—C(O)OZ', or a hydrogen atom;
Y' is chosen from the groups —C(O)OH, —C(O)OZ', —$CH_2$—CH(OH)—$SO_3H$ or —$CH_2$—CH(OH)—$SO_3$—Z';
Z' is chosen from a cationic counterion derived from an alkali metal or alkaline-earth metal, an ammonium ion or an ion derived from an organic amine; and
$R_{a''}$ is chosen from a $C_{10}$-$C_{30}$ alkyl or alkenyl group of an acid $R_a'$—C(O), an alkyl group, or an unsaturated $C_{17}$ group, or
the compounds of formula (B'2) below:

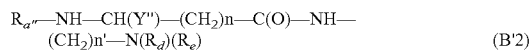
(B'2)

wherein:
Y" is chosen from —C(O)OH, —C(O)OZ", —CH$_2$—CH(OH)—SO$_3$H or —CH$_2$—CH(OH)—SO$_3$—Z";
R$_d$ and R$_e$ are chosen from, independently of each other, C$_1$-C$_4$ alkyl or hydroxyalkyl radical;
Z" is chosen from a cationic counterion derived from an alkali metal or alkaline-earth metal;
R$_a$" is chosen from a C$_{10}$-C$_{30}$ alkyl or alkenyl group of an acid R$_a$"C(O); and
n and n', independently of each other, are integers ranging from 1 to 3.

11. The composition according to claim 1, wherein the at least one second surfactant is chosen from:
oxyalkylenated (C$_8$-C$_{24}$)alkylphenols;
saturated or unsaturated, linear or branched, oxyalkylenated or glycerolated C$_8$-C$_{30}$ alcohols;
saturated or unsaturated, linear or branched, oxyalkylenated C$_8$-C$_{30}$ amides;
esters of saturated or unsaturated, linear or branched, C$_8$-C$_{30}$ acids and of polyethylene glycols;
esters of saturated or unsaturated, linear or branched, C$_8$-C$_{30}$ acids and of sorbitol, which are preferably oxyethylenated;
fatty acid esters of sucrose;
(C$_8$-C$_{30}$)alkylpolyglycosides, (C$_8$-C$_{30}$)alkenylpolyglycosides, which are optionally oxyalkylenated (0 to 10 oxyalkylene units) and which comprise 1 to 15 glucose units, (C$_8$-C$_{30}$)alkylglucoside esters;
saturated or unsaturated, oxyethylenated plant oils;
condensates of ethylene oxide and/or of propylene oxide, inter alia, alone or as mixtures;
N-(C$_8$-C$_{30}$)alkylglucamine derivatives and N-(C$_8$-C$_{30}$) acylmethylglucamine derivatives;
aldobionamides;
amine oxides;
oxyethylenated and/or oxypropylenated silicones; or mixtures thereof.

12. The composition according to claim 1, wherein the at least one second surfactant is chosen from alkyl sulfates, alkyl ether sulfates, alkylamido ether sulfates, alkylaryl polyether sulfates, monoglyceride sulfates, alkyl sulfonates, alkylamide sulfonates, alkylaryl sulfonates, alpha-olefin sulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyl taurates; salts of alkyl monoesters of polyglycoside-polycarboxylic acids, acyl lactylates, salts of D-galactosideuronic acids, salts of alkyl ether carboxylic acids, salts of alkylaryl ether carboxylic acids, salts of alkylamido ether carboxylic acids, or the corresponding non-salified forms thereof, the alkyl and acyl groups of all these compounds comprising from 6 to 40 carbon atoms, and the aryl group denoting a phenyl group; optionally oxyethylenated and comprising from 1 to 50 ethylene oxide units.

13. The composition according to claim 1, further comprising at least one aminoalkane sulfonic or sulfonothioic acid or a salt thereof, an amide derivative thereof or a functional analogue thereof chosen from the compounds of formula (A) or (B) below:

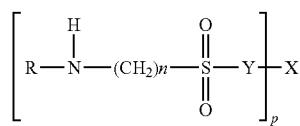

(A)

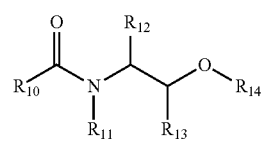

(B)

wherein:
R is a hydrogen;
Y is S or O;
X is chosen from hydrogen, a cation M$^{p+}$ of valency p, and an organic amine;
Z is chosen from hydrogen, a cation M$^{p+}$ of valency p, and an organic amine;
n is an integer greater than or equal to 2; and
p is an integer greater than or equal to 1.

14. The composition according to claim 13, wherein in formulae (A) and (B):
R is chosen from hydrogen, a linear C$_1$-C$_4$ alkyl radical and methyl;
p is 1 or 2;
n is 2 or 3;
X is chosen from hydrogen, a cation M$^{p+}$ chosen from alkali metals (K+, Na+), alkaline-earth metals (Mg$^{2+}$, Ca$^{2+}$) and ammonium ion; and
Z is chosen from hydrogen, a cation M$^{p+}$ chosen from alkali metals (K+, Na+), alkaline-earth metals (Mg$^{2+}$, Ca$^{2+}$) and ammonium ion.

15. The composition according to claim 13, comprising at least one of taurine, N-methyltaurine, thiotaurine, homotaurine, hypotaurine, or salts or mixtures thereof.

16. The composition according to claim 1, wherein the composition comprises at least one compound of ceramide type.

17. The composition according to claim 16, wherein the at least one compound of ceramide is chosen from the compounds of formula (C):

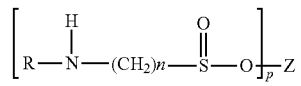

(C)

wherein:
R$_{10}$ is chosen from:
i) a linear or branched, saturated or unsaturated C$_1$-O$_{50}$ hydrocarbon-based radical, optionally substituted with one or more hydroxyl groups optionally esterified with an acid R$_{15}$COOH, wherein R$_{15}$ is a saturated or unsaturated, linear or branched, optionally mono- or polyhydroxylated C$_1$-C$_{35}$ hydrocarbon-based radical, the hydroxyl group(s) of the radical R$_{15}$ optionally esterified with a saturated or unsaturated, linear or branched, optionally mono- or polyhydroxylated C$_1$-C$_{35}$ fatty acid;
ii) a radical R"—(NR—CO)$_q$—R', with R chosen from a hydrogen atom or a mono- or polyhydroxylated C$_1$-C$_{20}$ hydrocarbon-based radical, R' and R" are hydrocarbon-based radicals comprising from 9 to 30 carbon atoms, R' is a divalent radical, and q is equal to 0 or 1; or iii) a radical $R_{16}$—O—CO—$(CH_2)_p$, where $R_{16}$ denotes a $C_1$-$C_{20}$ hydrocarbon-based radical and p is an integer ranging from 1 to 12;

$R_{11}$ is chosen from a hydrogen atom, a radical of saccharide type, a sulfate or phosphate residue, a phosphorylethylamine radical, or a phosphorylethylammonium radical, in which n is an integer ranging from 1 to 4, and m is an integer ranging from 1 to 8;

$R_{12}$ is chosen from a saturated or unsaturated, optionally hydroxylated $C_1$-$C_{33}$ hydrocarbon-based radical, the hydroxyl group(s) optionally esterified with a mineral acid or an acid $R_{15}$COOH, wherein $R_{15}$ is a saturated or unsaturated, linear or branched, optionally mono- or polyhydroxylated $C_1$-$C_{35}$ hydrocarbon-based radical, the hydroxyl group(s) optionally etherified with a (glycosyl)$_n$, (galactosyl)$_m$, sulfogalactosyl, phosphorylethylamine or phosphorylethylammonium radical, where $R_{12}$ may be optionally substituted with one or more $C_1$-$C_{14}$ alkyl radicals;

$R_{13}$ is chosen from a hydrogen atom, a saturated or unsaturated, linear or branched, optionally hydroxylated $C_3$-$O_{50}$ non-alkoxylated hydrocarbon-based radical, or a radical $R_{16}$—O—CO—$(CH_2)_p$, where $R_{16}$ is a $C_1$-$C_{20}$ hydrocarbon-based radical and p is an integer ranging from 1 to 12;

$R_{14}$ is chosen from a hydrogen atom or a saturated or unsaturated, linear or branched, optionally mono- or polyhydroxylated $C_1$-$C_{30}$ hydrocarbon-based radical, the hydroxyl group(s) optionally etherified with a (glycosyl)$_n$, (galactosyl)$_m$, sulfogalactosyl, phosphorylethylamine or phosphorylethylammonium radical.

18. The composition according to claim 17, wherein the at least one compound of ceramide type is of formula (C) wherein $R_{10}$ is a $C_{12}$-$C_{20}$ alkenyl chain comprising one or two double bonds; $R_{11}$ is a hydrogen atom; $R_{12}$ is an optionally hydroxylated linear $C_{11}$-$C_{17}$ radical; $R_{13}$ is a $C_{10}$-$C_{20}$ alkyl group, and $R_{14}$ is a hydrogen atom.

19. The composition according to claim 17, wherein the at least one compound of ceramide type is chosen from:
2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol and in particular N-stearoylphytosphingosine,
2-N-palmitoylaminohexadecane-1,3-diol; or
mixtures thereof.

20. The composition according to claim 1, wherein the composition further comprises at least one oxidizing agent other than atmospheric oxygen.

21. The composition according to claim 20, wherein the at least one oxidizing agent other than atmospheric oxygen is in the form of a foam.

22. A process for dyeing keratin fibers, comprising:
(a) preparing a cosmetic mixture by mixing:
a dye composition comprising:
at least one oxidation dye precursor;
at least one amphoteric or zwitterionic surfactant;
at least one second surfactant chosen from nonionic surfactants, anionic surfactants, or mixtures thereof;
at least one fatty substance other than ceramides chosen from liquid petroleum jelly, C6-C16 alkanes, polydecenes, or esters of fatty acids or of fatty alcohols, which are liquid, or mixtures thereof; and
at least one nonionic guar gum chosen from modified nonionic guar gums modified with C1-C6 hydroxyalkvl groups; with
a composition comprising at least one oxidizing agent other than atmospheric oxygen; and
(b) applying said mixture to said keratin fibers,
wherein said mixture is in the form of a foam.

23. An aerosol device comprising:
(a) a composition for dyeing human keratin fibers comprising:
at least one oxidation dye precursor;
at least one amphoteric or zwitterionic surfactant;
at least one second surfactant chosen from nonionic surfactants, anionic surfactants, or mixtures thereof;
at least one fatty substance other than ceramides chosen from liquid petroleum jelly, C6-C16 alkanes, polydecenes, or esters of fatty acids or of fatty alcohols, which are liquid, or mixtures thereof; and
at least one nonionic guar gum chosen from modified nonionic guar gums modified with C1-C6hydroxyalkvl groups; and
(b) a means for dispensing the composition in the form of a foam.

24. The aerosol device of claim 23, comprising either at least one container equipped with two pouches or at least two containers.

* * * * *